United States Patent
Kim et al.

(10) Patent No.: US 9,634,257 B2
(45) Date of Patent: Apr. 25, 2017

(54) HETEROCYCLIC COMPOUND AND ORGANIC LIGHT-EMITTING DEVICE INCLUDING THE SAME

(71) Applicants: SAMSUNG DISPLAY CO., LTD., Yongin, Gyeonggi-Do (KR); SEOUL NATIONAL UNIVERSITY R&DB FOUNDATION, Gwanak-Gu, Seoul (KR)

(72) Inventors: Se-Hun Kim, Yongin (KR); Mi-Kyung Kim, Yongin (KR); Jong-In Hong, Seoul (KR); Dong-Hyun Kim, Yongin (KR); Seong-Jin Jeong, Seoul (KR); Hwan-Hee Cho, Yongin (KR); Chang-Woong Chu, Yongin (KR)

(73) Assignees: Samsung Display Co., Ltd., Yongin-si (KR); Seoul National University R&DB Foundation, Seoul (KR)

( * ) Notice: Subject to any disclaimer, the term of this patent is extended or adjusted under 35 U.S.C. 154(b) by 496 days.

(21) Appl. No.: 14/224,015

(22) Filed: Mar. 24, 2014

(65) Prior Publication Data
US 2015/0034917 A1 Feb. 5, 2015

(30) Foreign Application Priority Data
Jul. 30, 2013 (KR) .................. 10-2013-0090425

(51) Int. Cl.
| H01L 51/50 | (2006.01) |
|---|---|
| H01L 51/00 | (2006.01) |
| C09K 11/06 | (2006.01) |
| C07D 401/10 | (2006.01) |
| C07D 235/14 | (2006.01) |

(52) U.S. Cl.
CPC .......... H01L 51/006 (2013.01); C07D 235/14 (2013.01); C07D 401/10 (2013.01); C09K 11/06 (2013.01); H01L 51/0061 (2013.01); H01L 51/0072 (2013.01); H01L 2251/308 (2013.01)

(58) Field of Classification Search
None
See application file for complete search history.

(56) References Cited

U.S. PATENT DOCUMENTS

| 5,635,308 | A | 6/1997 | Inoue et al. | |
|---|---|---|---|---|
| 7,507,485 | B2* | 3/2009 | Oh .................... | H01L 51/0058 313/504 |
| 8,785,002 | B1* | 7/2014 | Anzenbacher, Jr. . | C07D 235/18 252/301.16 |
| 2006/0086938 | A1* | 4/2006 | Kang .................. | G02F 1/1345 257/72 |
| 2007/0200490 | A1 | 8/2007 | Kawamura et al. | |
| 2011/0260153 | A1 | 10/2011 | In et al. | |
| 2012/0179089 | A1* | 7/2012 | Sisk ..................... | C07D 401/04 604/20 |
| 2012/0298966 | A1* | 11/2012 | Zeng .................. | C07F 7/08 257/40 |
| 2013/0032787 | A1* | 2/2013 | Kim .................... | C07D 401/04 257/40 |
| 2013/0069523 | A1 | 3/2013 | Matsuura et al. | |

FOREIGN PATENT DOCUMENTS

| JP | 07-138561 | 5/1995 |
|---|---|---|
| JP | 8-12600 | 1/1996 |
| JP | 08-239655 | 9/1996 |
| JP | 2658463 B2 | 9/1997 |
| JP | 2000-095766 A * | 4/2000 |
| KR | 10-2005-0019907 | 3/2005 |
| KR | 10-2009-0111355 | 10/2009 |
| KR | 10-1018547 | 3/2011 |
| KR | 10-1031463 | 4/2011 |
| KR | 10-2011-0123701 | 11/2011 |
| KR | 10-2012-0013917 | 2/2012 |
| KR | 10-2012-0083241 | 7/2012 |
| KR | 10-2012-0101558 | 9/2012 |
| KR | 10-1191669 | 10/2012 |

OTHER PUBLICATIONS

Machine translation for JP 2000-095766 A (publication date: Apr. 2000).*
Angew. Chem. Int. Ed. (2008), vol. 47, pp. 581-585.*
Chemistry of Materials, vol. 21, No. 12, (2009), pp. 2452-2458.*
Jeong, et al., Efficient deep-blue emitters based on triphenylamine-linked benzimidazole derivatives for nondoped fluorescent organic light-emitting diodes, Organic Electronics, Organic Electronics 14 (2013), pp. 2497-2504, Elsevier.
Tang, C.W., et al., *Organic electroluminescent diodes*, Applied Physics Letters, Sep. 21, 1987, vol. 51, No. 12, pp. 913-915.
Patent Abstracts of Japan for Japanese Publication 03-200289, dated Sep. 2, 1991, corresponding to Japanese Patent 2658463 dated Sep. 30, 1997, (1 page).

* cited by examiner

*Primary Examiner* — Dawn Garrett
(74) *Attorney, Agent, or Firm* — Lewis Roca Rothgerber Christie LLP

(57) ABSTRACT

A heterocyclic compound of Formula 1 below and an organic light-emitting device including the same are provided.

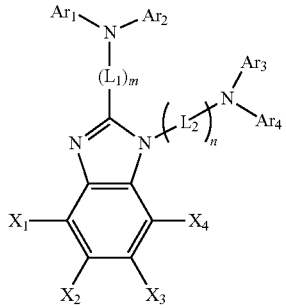

Formula 1

$X_1$ to $X_4$, $L_1$, $L_2$, n, m, and $Ar_1$ to $Ar_4$ in Formula 1 are defined as in the specification.

21 Claims, 1 Drawing Sheet

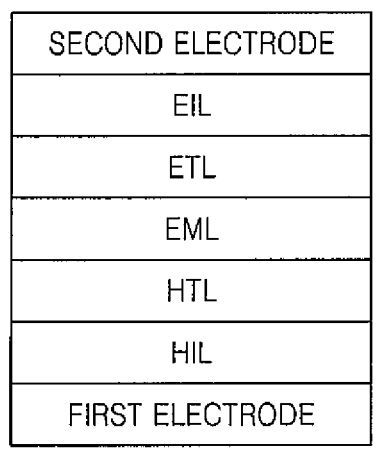

HETEROCYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2013-0090425, filed on Jul. 30, 2013, in the Korean Intellectual Property Office, the disclosure of which is incorporated herein in its entirety by reference.

BACKGROUND

1. Field

One or more embodiments of the present invention relate to a heterocyclic compound and an organic light-emitting device including the same.

2. Description of the Related Art

Organic light-emitting devices (OLEDs), which are self-emitting devices, have advantages such as wide viewing angles, excellent contrast, quick response, high brightness, excellent driving voltage characteristics, and multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is an ongoing demand for a material having improved electrical stability, high charge-transport or emission capability, and a high glass transition temperature that is high enough to prevent crystallization, in regard to existing small molecule materials.

SUMMARY

Aspects of one or more embodiments of the present invention are directed toward a novel heterocyclic compound.

Aspects of one or more embodiments of the present invention are directed toward an organic light-emitting device including the heterocyclic compound in an emission layer, and thus having a high efficiency and improved lifetime characteristics.

Additional aspects will be set forth in part in the description which follows and, in part, will be apparent from the description, or may be learned by practice of the presented embodiments.

According to one or more embodiments of the present invention, a heterocyclic compound is represented by Formula 1 below:

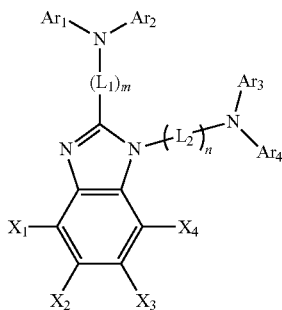

Formula 1 wherein, in Formula 1 above, $X_1$ to $X_4$ are each independently a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C3-C10 cycloalkenyl group, a substituted or unsubstituted C3-C10 heterocycloalkyl group, a substituted or unsubstituted C3-C10 heterocycloalkenyl group, a substituted or unsubstituted C6-C60 aryl group, a substituted or unsubstituted C6-C60 aryloxy group, a substituted or unsubstituted C6-C60 arylthiol group, a substituted or unsubstituted C2-C60 heteroaryl group, —N($Q_1$)($Q_2$), or —Si($Q_3$)($Q_4$)($Q_5$), where $Q_1$ to $Q_6$ are each independently a hydrogen atom, a C1-C10 alkyl group, a C6-C20 aryl group, or a C2-C20 heteroaryl group;

$L_1$ and $L_2$ are each independently a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, or a substituted or unsubstituted C2-C60 heteroarylene group;

n and m are each independently an integer from 1 to 3; and $Ar_1$ to $Ar_4$ are each independently a substituted or unsubstituted C6-C60 aryl group, or a substituted or unsubstituted C2-C60 heteroaryl group.

According to one or more embodiments of the present invention, an organic light-emitting device includes: a first electrode; a second electrode; and an organic layer between the first electrode and the second electrode, wherein the organic layer includes the above-described heterocyclic compound of Formula 1.

According to one or more embodiments of the present invention, a flat panel display device includes the above-described organic light-emitting device, wherein the first electrode of the organic light-emitting device is electrically connected to a source electrode or a drain electrode of a thin-film transistor.

BRIEF DESCRIPTION OF THE DRAWING

These and/or other aspects will become apparent and more readily appreciated from the following description of the embodiments, taken in conjunction with the accompanying drawing of which:

The drawing is a schematic view of a structure of an organic light-emitting device according to an embodiment of the present invention.

DETAILED DESCRIPTION

Reference will now be made in more detail to embodiments, examples of which are illustrated in the accompanying drawing, wherein like reference numerals refer to the like elements throughout. In this regard, the present embodiments may have different forms and should not be construed as being limited to the descriptions set forth herein. Accordingly, the embodiments are merely described below, by referring to the drawing, to explain aspects of the present description. As used herein, the term "and/or" includes any and all combinations of one or more of the associated listed items. Expressions such as "at least one of," when preceding a list of elements, modify the entire list of elements and do not modify the individual elements of the list. Further, the use of "may" when describing embodiments of the present invention refers to "one or more embodiments of the present invention."

According to an embodiment of the present invention, a heterocyclic compound is represented by Formula 1 below:

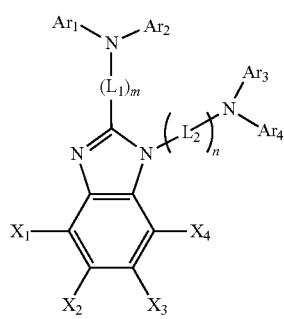

Formula 1

In Formula 1 above, $X_1$ to $X_4$ may be each independently a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C3-C10 cycloalkenyl group, a substituted or unsubstituted C3-C10 heterocycloalkyl group, a substituted or unsubstituted C3-C10 heterocycloalkenyl group, a substituted or unsubstituted C6-C60 aryl group, a substituted or unsubstituted C6-C60 aryloxy group, a substituted or unsubstituted C6-C60 arylthiol group, a substituted or unsubstituted C2-C60 heteroaryl group, —N($Q_1$)($Q_2$), or —Si($Q_3$)($Q_4$)($Q_5$), where $Q_1$ to $Q_5$ are each independently a hydrogen atom, a C1-C10 alkyl group, a C6-C20 aryl group, or a C2-C20 heteroaryl group;

$L_1$ and $L_2$ may be each independently a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, or a substituted or unsubstituted C2-C60 heteroarylene group;

n and m may be each independently an integer from 1 to 3; and $Ar_1$ to $Ar_4$ may be each independently a substituted or unsubstituted C6-C60 aryl group, or a substituted or unsubstituted C2-C60 heteroaryl group.

An organic light-emitting device is a self-emitting device based on the principle that light is emitted from a fluorescent material by the recombination energy of holes injected via a cathode and electrons injected via an anode (generated when a voltage is applied). Since the development of a low-voltage organic light-emitting device having a stacked structure by C. W. Tang of Eastman Kodak Company, there has been active research into organic light-emitting devices using organic materials. C. W. Tang et al. suggested the use of tris(8-hydroxy quinolinolato aluminum) in an emission layer and triphenyldiamine derivative in a hole transport layer. An organic light-emitting device having a stacked structure may have a higher efficiency of hole injection into the emission layer, may effectively block electrons injected via the anode to increase efficiency of exciton generation by the recombination of holes and electrons, and may have the ability to confine excitons in the emission layer. A two-layered structure including a hole transport (and/or injection) layer and an electron transport layer, and a three-layered structure including a hole transport (and/or injection) layer, an emission layer, and an electron transport (and/or injection) layer are suitable structures for organic light-emitting device. Regarding organic light-emitting devices with such stacked structures, research into new device structures or manufacturing methods have been conducted to increase the hole-electron recombination efficiency.

Suitable light-emitting materials for organic light-emitting devices are chelate complexes, such as tris(8-quinolinolato)aluminum complex, coumarin derivatives, tetraphenyl butadiene derivatives, bis-styrylarylene derivatives, and oxadiazole derivatives, which have been reported to emit from blue to red visible-range light, raising expectations for full-color display devices. An organic light-emitting device using a phenylanthracene derivative as a light-emitting material has also been disclosed. Such anthracene derivative may be used as a blue light-emitting material.

In general, a benzimidazole moiety may have electron transport characteristics. According to embodiments of the present invention, the heterocyclic compound of Formula 1 above has both such a benzimidazole moiety having electron transport characteristics and an arylamine group having hole transport characteristics, and thus may serve as an amphoteric light-emitting material.

Therefore, an organic light-emitting device including the heterocyclic compound of Formula 1 above may have high efficiency and improved lifetime characteristics. According to embodiments, the heterocyclic compound of Formula 1 above may be used in a full-color display.

Substituents of the compound of Formula 1 will be described in greater detail.

In some embodiments, $X_1$ to $X_4$ in Formula 1 may be each independently a hydrogen atom or a deuterium atom.

In some embodiments, n and m in Formula 1 may be each independently 1 or 2.

In some embodiments, $L_1$ and $L_2$ in Formula 1 may be each independently a group represented by Formula 2a below:

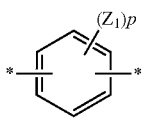

In Formula 2a, $Z_1$ may be a hydrogen atom, a deuterium atom, a substituted or unsubstituted C1-C20 alkyl group, a substituted or unsubstituted C6-C20 aryl group, a substituted or unsubstituted C2-C20 heteroaryl group, a substituted or unsubstituted C6-C20 condensed polycyclic group, a halogen atom, a cyano group, a nitro group, a hydroxy group, a carboxy group, or $Si(Q_3)(Q_4)(Q_5)$, where $Q_3$ to $Q_5$ may be each independently a hydrogen atom, a C1-C10 alkyl group, a C6-C20 aryl group, or a C2-C20 heteroaryl group;

p may be an integer from 1 to 4, and when p is 2 or more, a plurality of $Z_1$s are identical to or different from each other; and

* indicates a binding site.

In some embodiments, $Z_1$ in Formula 2a may be a hydrogen atom or a deuterium atom.

In some other embodiments, $Ar_1$ to $Ar_4$ in Formula 1 may be each independently a group represented by Formula 3a or 3b below:

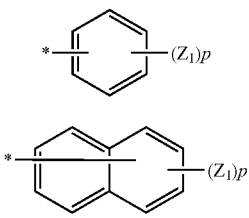

In Formulae 3a and 3b, $Z_1$ may be a hydrogen atom, a deuterium atom, a substituted or unsubstituted C1-C20 alkyl group, a substituted or unsubstituted C6-C20 aryl group, a substituted or unsubstituted C2-C20 heteroaryl group, a substituted or unsubstituted C6-C20 condensed polycyclic group, a halogen atom, a cyano group, a nitro group, a hydroxy group, a carboxy group, or $Si(Q_3)(Q_4)(Q_5)$, where $Q_3$ to $Q_5$ may be each independently a hydrogen atom, a C1-C10 alkyl group, a C6-C20 aryl group, or a C2-C20 heteroaryl group;

p may be an integer from 1 to 7, and when p is two or more, a plurality of $Z_1$s are identical to or different from each other; and

* indicates a binding site.

Hereinafter, substituents described with reference to the formulae will now be described in more detail. In this regard, the numbers of carbons in substituents are presented only for illustrative purposes and do not limit the characteristics of the substituents. The substituents not defined herein are construed as having the same meanings understood by one of ordinary skill in the art.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. At least one hydrogen atom of the alkyl group may be substituted with a deuterium atom, a halogen atom, a hydroxyl group, a nitro group, a cyano group, an amino group, an amidino group, a hydrazine, a hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, an alkylsilyl group, an arylsilyl group, or a C4-C16 heteroaryl group.

The unsubstituted C2-C60 alkenyl group indicates an unsaturated alkyl group having at least one carbon-carbon double bond in the center or at a terminal of the alkyl group. Examples of the alkenyl group are an ethenyl group, a propenyl group, and a butenyl group. At least one hydrogen atom in the unsubstituted alkenyl group may be substituted with a substituent described above in conjunction with the alkyl group.

The unsubstituted C2-C60 alkynyl group indicates an alkyl group having at least one carbon-carbon triple bond in the center or at a terminal of the alkyl group. Non-limiting examples of the unsubstituted C2-C20 alkynyl group are acetylene, propynyl, phenylacetylene, naphthylacetylene, isopropylacetylene, t-butylacetylene, and diphenylacetylene. At least one hydrogen atom in the alkynyl group may be substituted with a substituent described above in conjunction with the alkyl group.

The unsubstituted C3-C60 cycloalkyl group indicates a C3-C60 cyclic alkyl group wherein at least one hydrogen atom in the cycloalkyl group may be substituted with a substituent described above in conduction with the C1-C60 alkyl group.

The unsubstituted C1-C60 alkoxy group indicates a group having a structure of —OA wherein A is an unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. At least one hydrogen atom of the alkoxy group may be substituted with a substituent such as those described above in conjunction with the alkyl group.

The unsubstituted C6-C60 aryl group indicates a carbocyclic aromatic system containing at least one ring. At least two rings may be fused to each other or linked to each other by a single bond. The term 'aryl' refers to an aromatic system, such as phenyl, naphthyl, or anthracenyl. At least one hydrogen atom in the aryl group may be substituted with a substituent described above in conjunction with the unsubstituted C1-C60 alkyl group.

Non-limiting examples of the substituted or unsubstituted C6-C60 aryl group are a phenyl group, a C1-C10 alkylphenyl group (for example, an ethylphenyl group), a biphenyl group, a C1-C10 alkyl biphenyl group, a C1-C10 alkoxybiphenyl group, a o-, m-, and p-toryl group, an o-, m-, and p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, a methylnaphthyl group), a C1-C10 alkoxynaphthyl group (for example, a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coronelyl group, a trinaphthylenyl group, a heptaphenyl group, a heptacenyl group, a pyranthrenyl group, and an ovalenyl group.

The unsubstituted C2-C60 heteroaryl group used herein includes one, two, three, or four heteroatoms selected from N, O, P or S. At least two rings may be fused to each other or linked to each other by a single bond. Non-limiting examples of the unsubstituted C2-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. In addition, at least one hydrogen atom in the heteroaryl group may be substituted with a substituent described above in conjunction with the unsubstituted C1-C60 alkyl group.

The unsubstituted C6-C60 aryloxy group is a group represented by —OA$_1$, wherein A$_1$ may be a C6-C60 aryl group. An example of the aryloxy group is a phenoxy group. At least one hydrogen atom in the aryloxy group may be substituted with a substituent described above in conjunction with the unsubstituted C1-C60 alkyl group.

The unsubstituted C6-C60 arylthio group is a group represented by —SA$_1$, wherein A$_1$ may be a C5-C60 aryl group. Non-limiting examples of the arylthio group are a benzenethio group and a naphthylthio group. At least one hydrogen atom in the arylthio group may be substituted with a substituent described above in conjunction with the unsubstituted C1-C60 alkyl group.

The unsubstituted C6-C60 (for example, C6-C20) condensed polycyclic group used herein refers to a substituent including at least two rings wherein at least one aromatic ring and/or at least one non-aromatic ring are fused to each other, or refers to a substituent having an unsaturated group in a ring that may not form a conjugate structure. The unsubstituted C6-C60 condensed polycyclic group is distinct from an aryl group or a heteroaryl group in terms of being non-aromatic.

Non-limiting examples of the heterocyclic compound of Formula 1 above are Compounds 1 to 34 below.

Compound 1

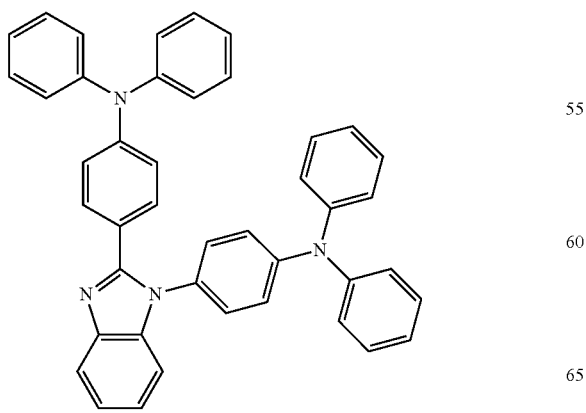

Compound 2

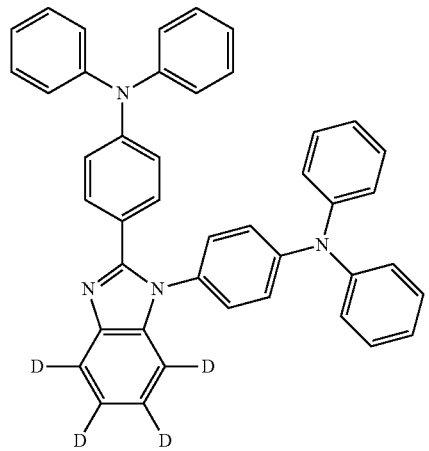

Compound 3

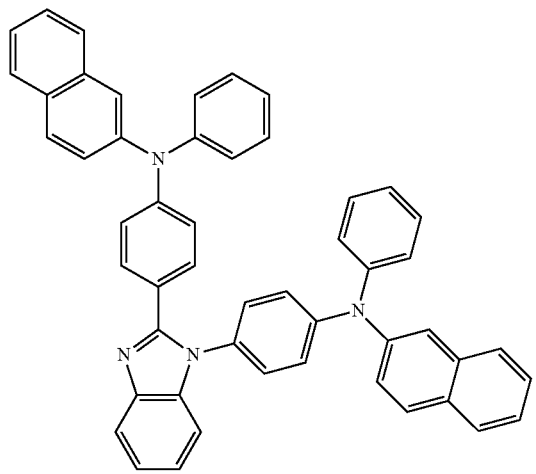

Compound 4

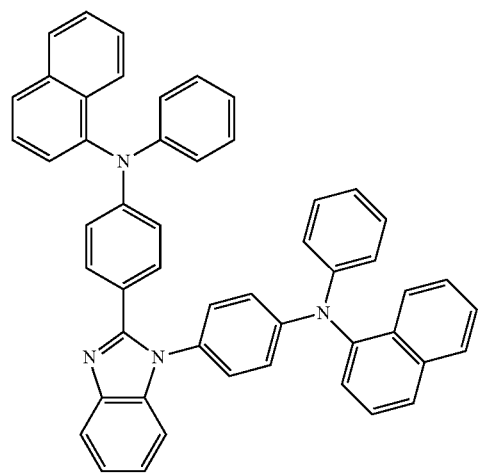

Compound 5
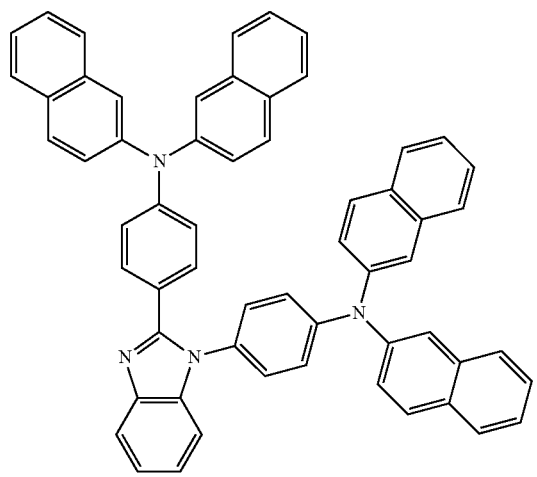
Compound 6
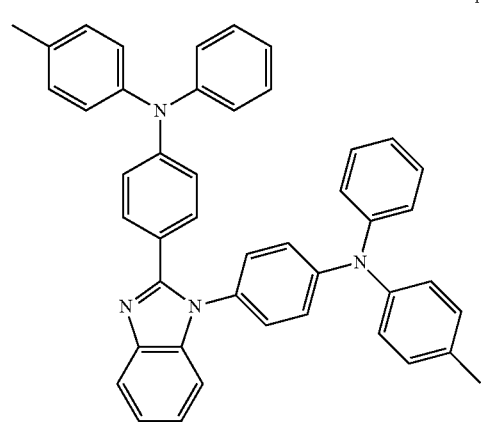
Compound 7
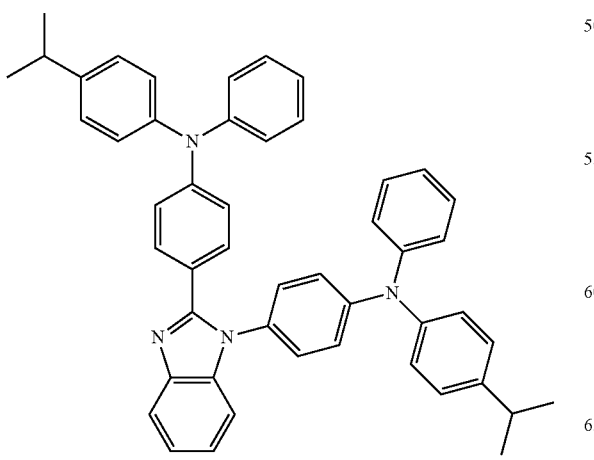
Compound 8
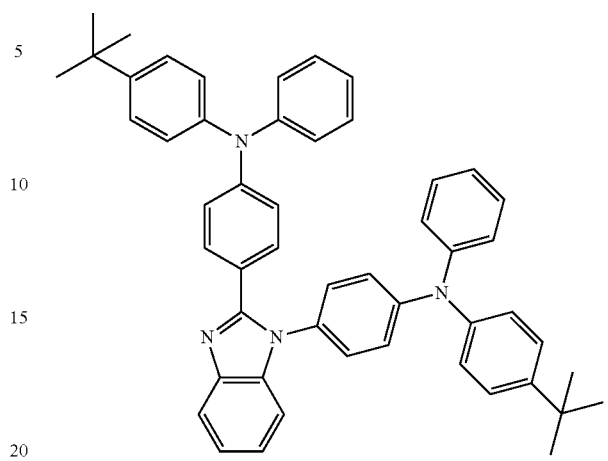
Compound 9
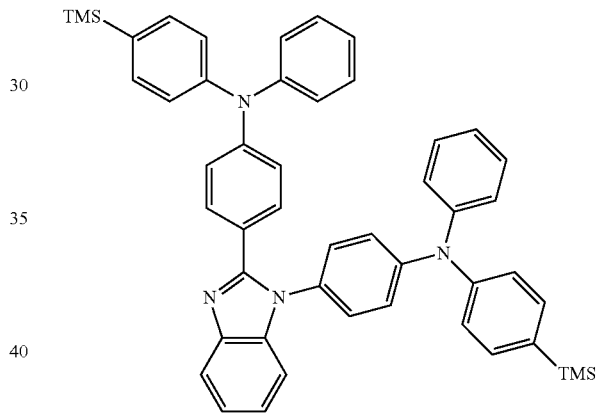
Compound 10
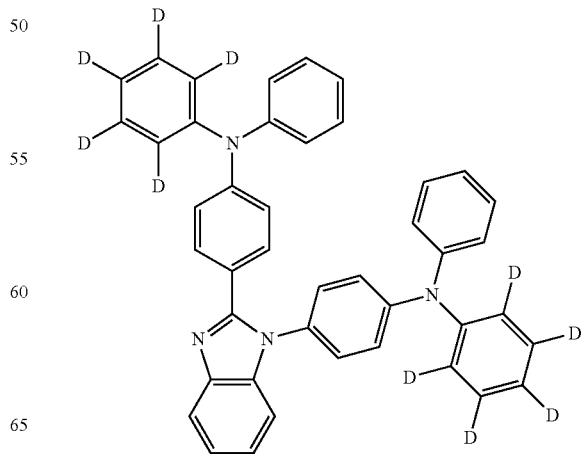

-continued
Compound 11
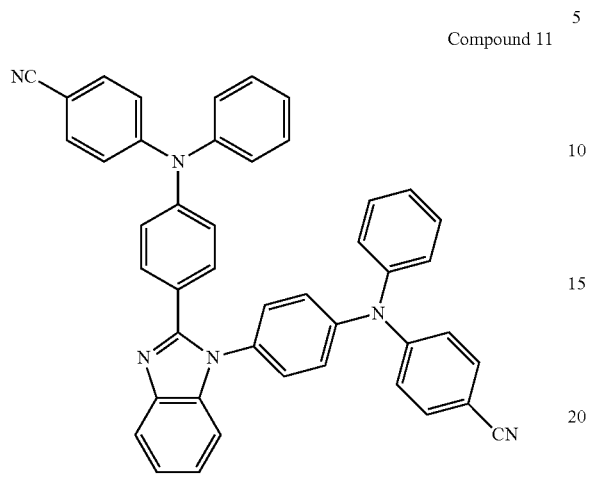
Compound 12
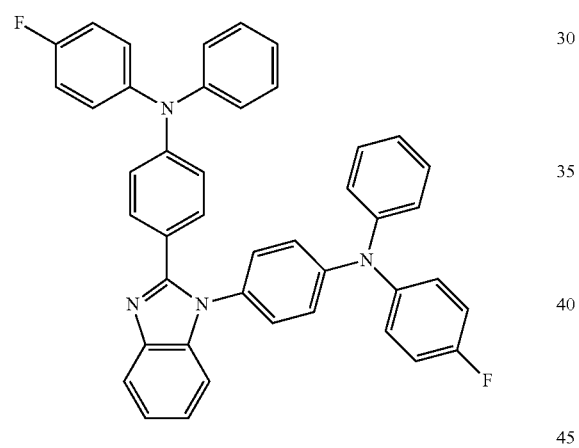
Compound 13
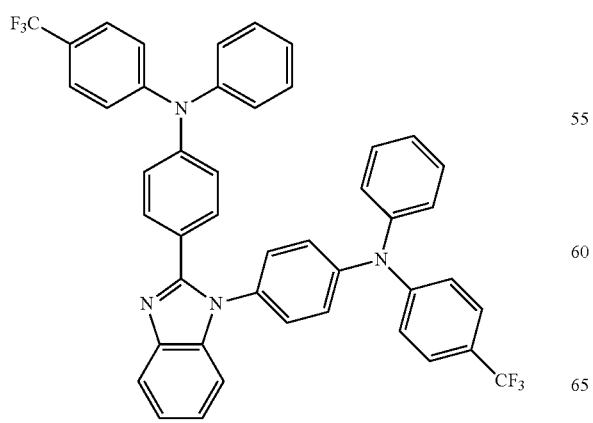
-continued
Compound 14
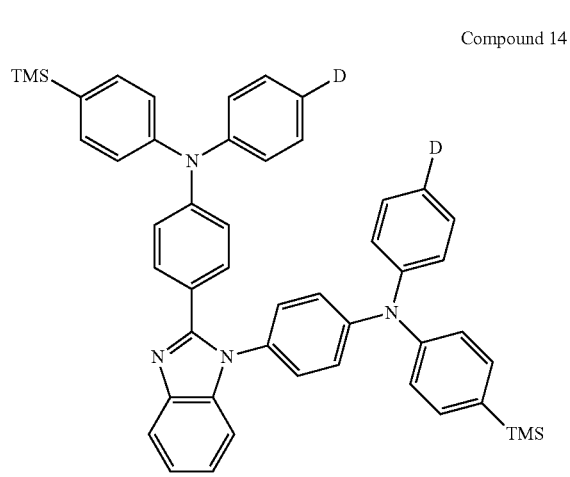
Compound 15
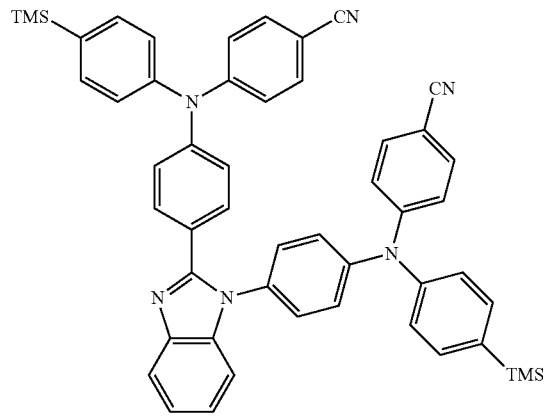
Compound 16
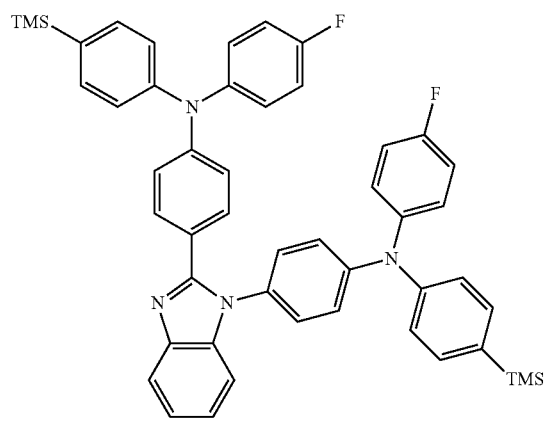

Compound 17
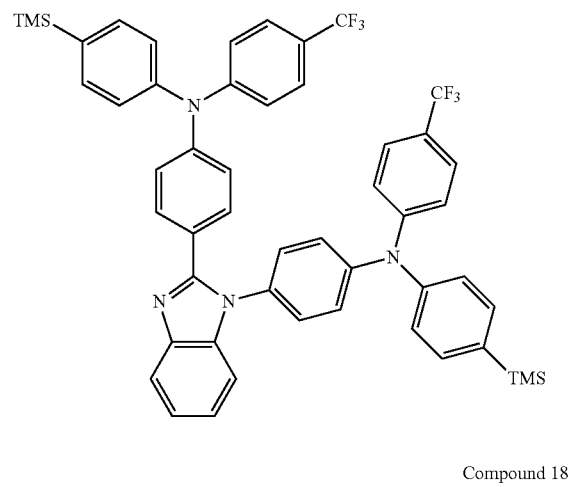
Compound 18
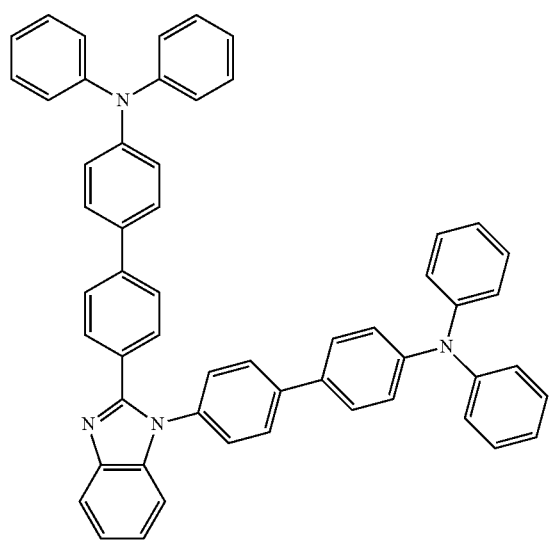
Compound 19
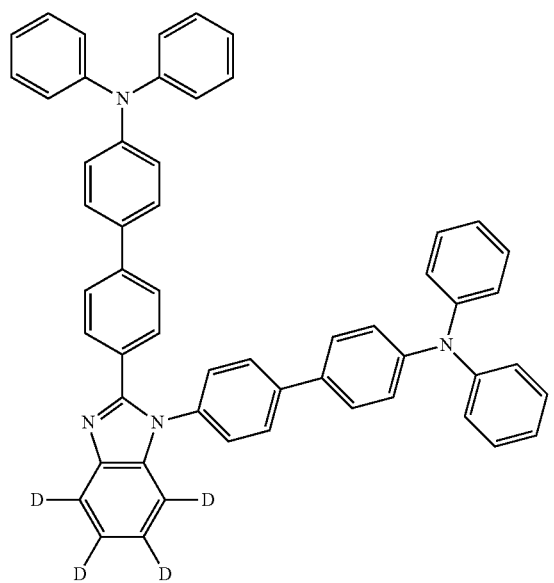
Compound 20
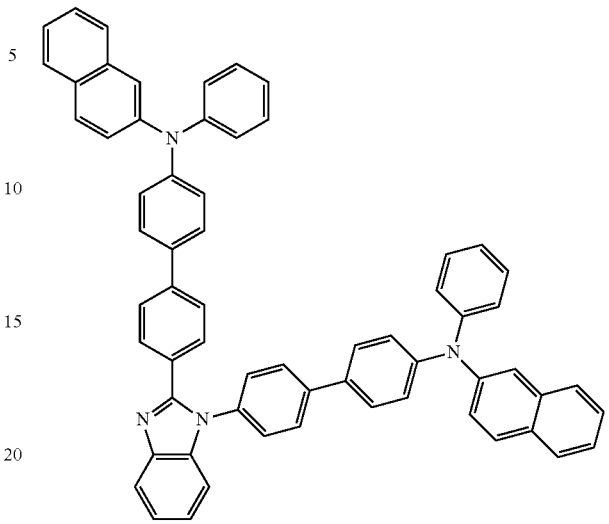
Compound 21
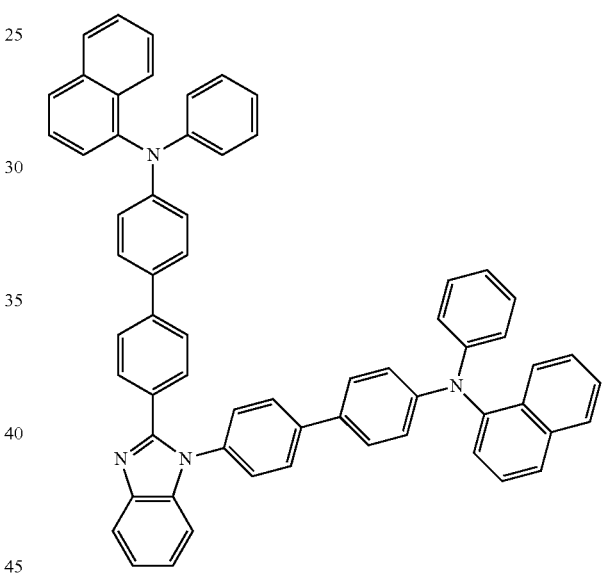
Compound 22
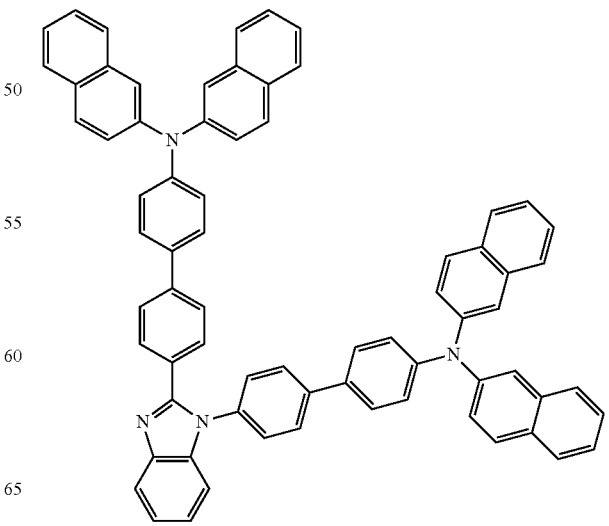

Compound 23
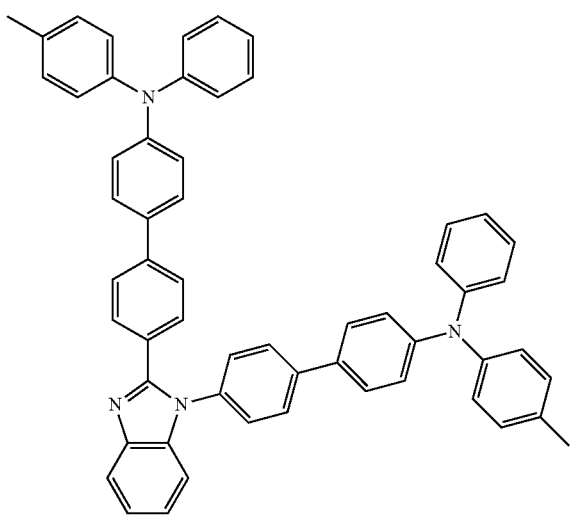
Compound 24
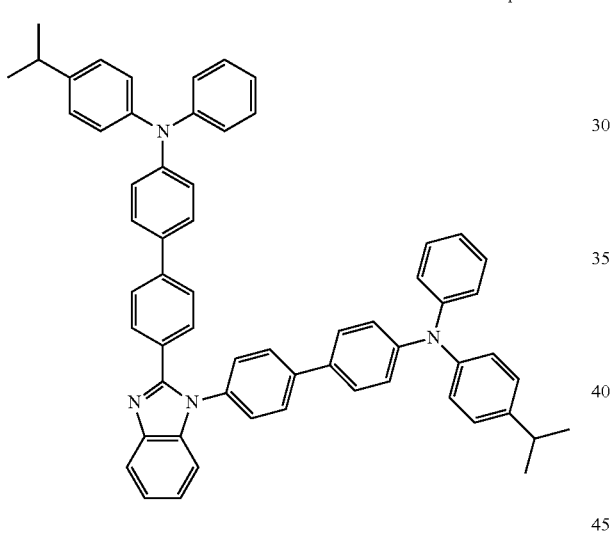
Compound 25
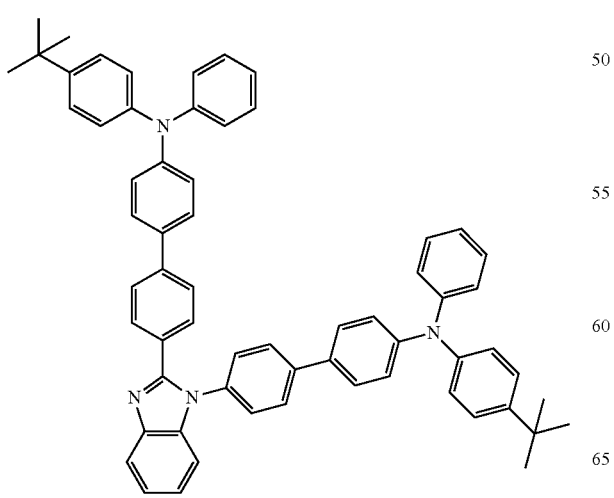
Compound 26
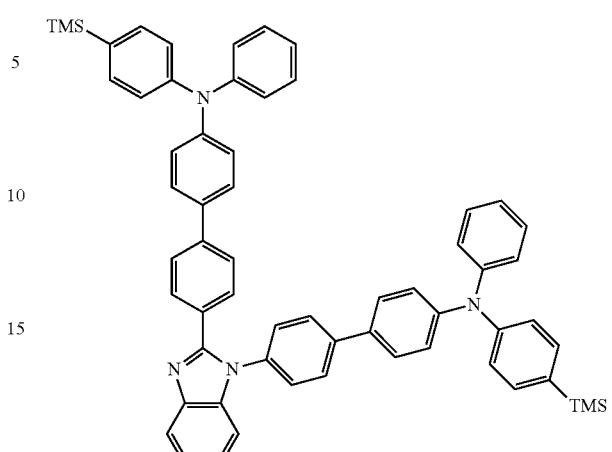
Compound 27
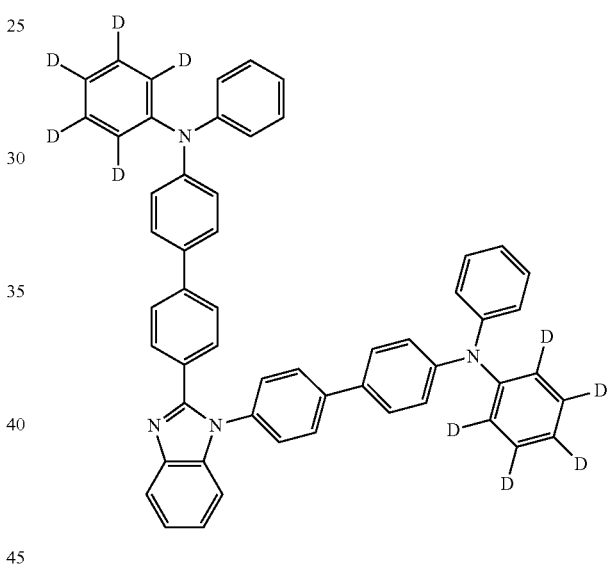
Compound 28
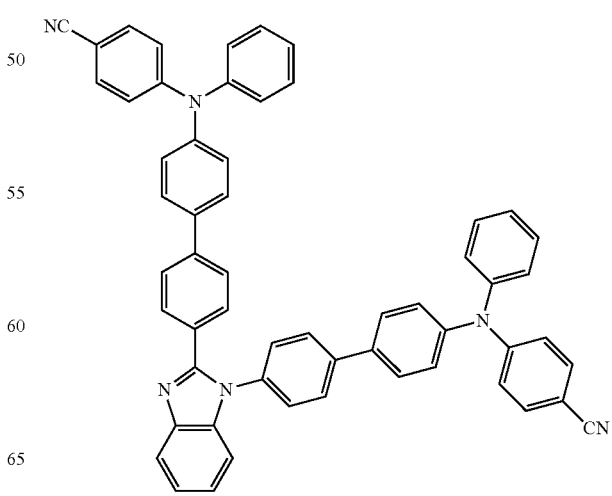

Compound 29

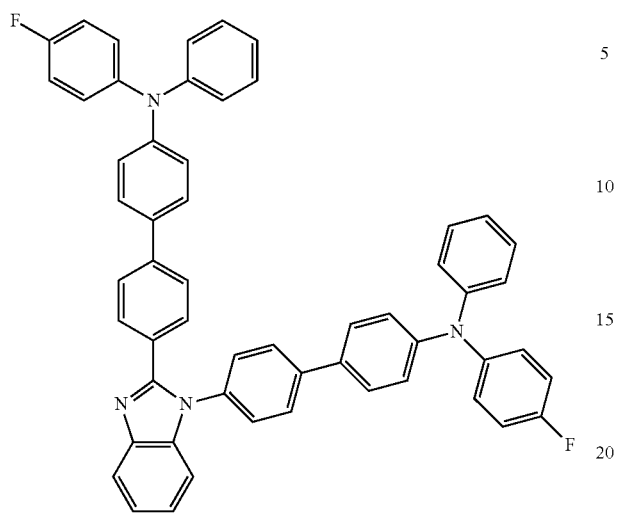

[Compound 30]

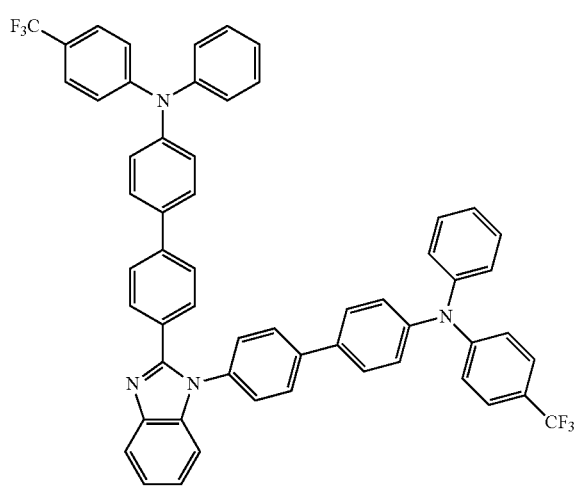

Compound 31

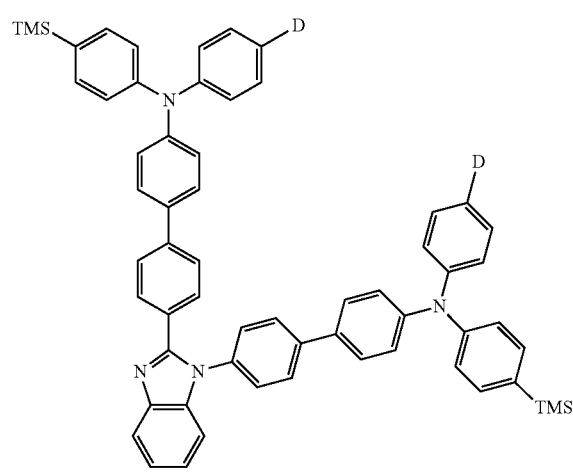

Compound 32

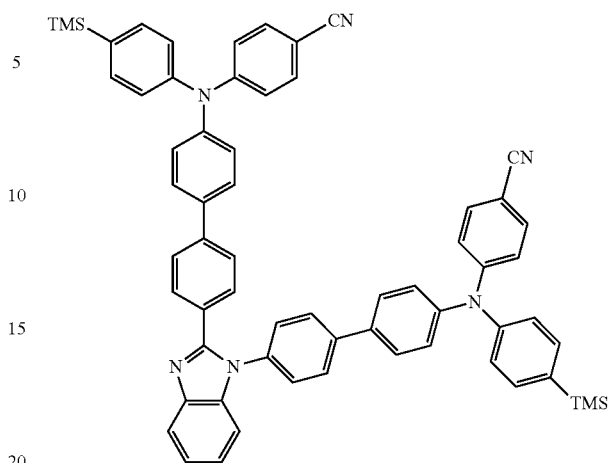

Compound 33

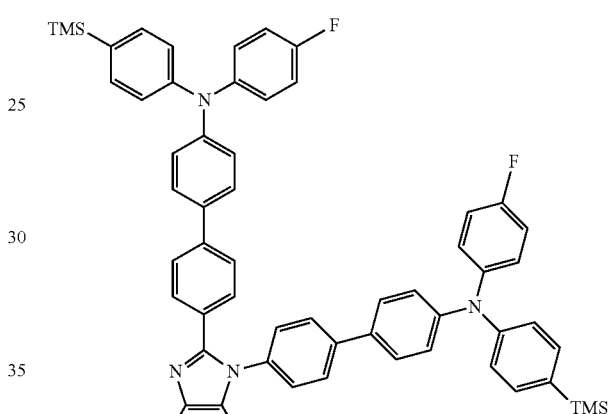

Compound 34

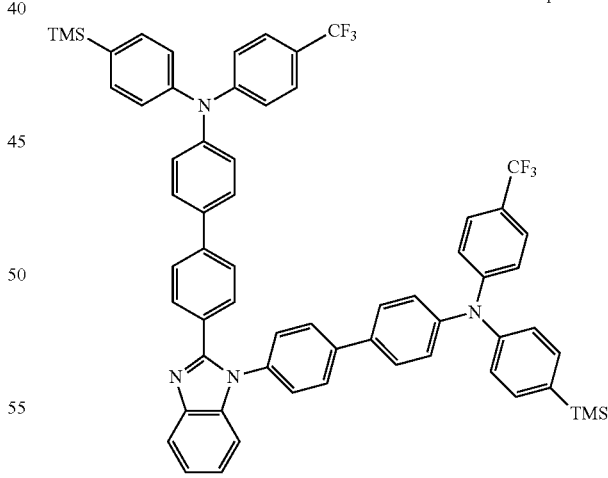

According to another embodiment of the present invention, an organic light-emitting device includes a first electrode, a second electrode, and an organic layer disposed between the first electrode and the second electrode, wherein the organic layer includes the heterocyclic compound of Formula 1 above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

For example, the organic layer may be an emission layer, for example, a blue emission layer.

In some embodiments, the organic layer may include an electron injection layer, an electron transport layer, a functional layer having both electron injection and transport capabilities, an emission layer, a hole injection layer, a hole transport layer, or a functional layer having both hole injection and transport capabilities, and the emission layer may include an anthracene-based compound, an arylamine-based compound or a styryl-based compound.

In some other embodiments, the organic layer may include an electron injection layer, an electron transport layer, a functional layer having both electron injection and transport capabilities, an emission layer, a hole injection layer, a hole transport layer, or a functional layer having both hole injection and transport capabilities; at least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material.

In some embodiments, the charge-generating material may be a p-type dopant, and the p-type dopant may be a quinine derivative, a metal oxide or a cyano group-containing compound.

In some embodiments, the organic layer may include an electron transport layer, and the electron transport layer may include an electron-transporting organic compound and a meta complex.

The metal complex may be a lithium (Li) complex.

The term "organic layer" as used herein refers to a single layer and/or a plurality of layers disposed between the first and second electrodes of the organic light-emitting device.

The drawing is a schematic sectional view of an organic light-emitting device according to an embodiment of the present invention.

Hereinafter, a structure of an organic light-emitting device according to an embodiment of the present invention and a method of manufacturing the same will now be described with reference to the drawing.

A substrate may be any suitable substrate that is used in existing organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate.

When the first electrode is an anode, a material having a high work function may be used as the first electrode-forming material to facilitate hole injection. The first electrode may be a reflective electrode or a transmission electrode. Transparent and conductive materials such as ITO, IZO, $SnO_2$, or ZnO may be used to form the first electrode. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer(s) is disposed on the first electrode. The organic layer may include a hole injection layer (HIL), a hole transport layer (HTL), a buffer layer, an emission layer (EML), an electron transport layer (ETL), or an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary depending on the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary depending on the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

The HIL may be formed of any suitable material that is commonly used to form an HIL. Non-limiting examples of the material that can be used to form the HIL are N,N'-diphenyl-N,N'-bis-[4-(phenyl-m-tolyl-amino)-phenyl]-biphenyl-4,4'-diamine, DNTPD, a phthalocyanine compound (such as copperphthalocyanine), 4,4',4"-tris(3-methylphenylphenylamino)triphenylamine (m-MTDATA), N,N'-di(1-naphthyl)-N,N'-diphenylbenzidine (NPB), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline/poly(4-styrenesulfonate) (PANI/PSS).

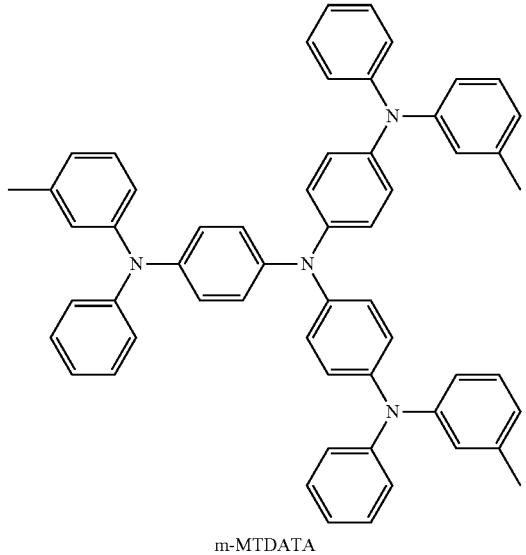

m-MTDATA

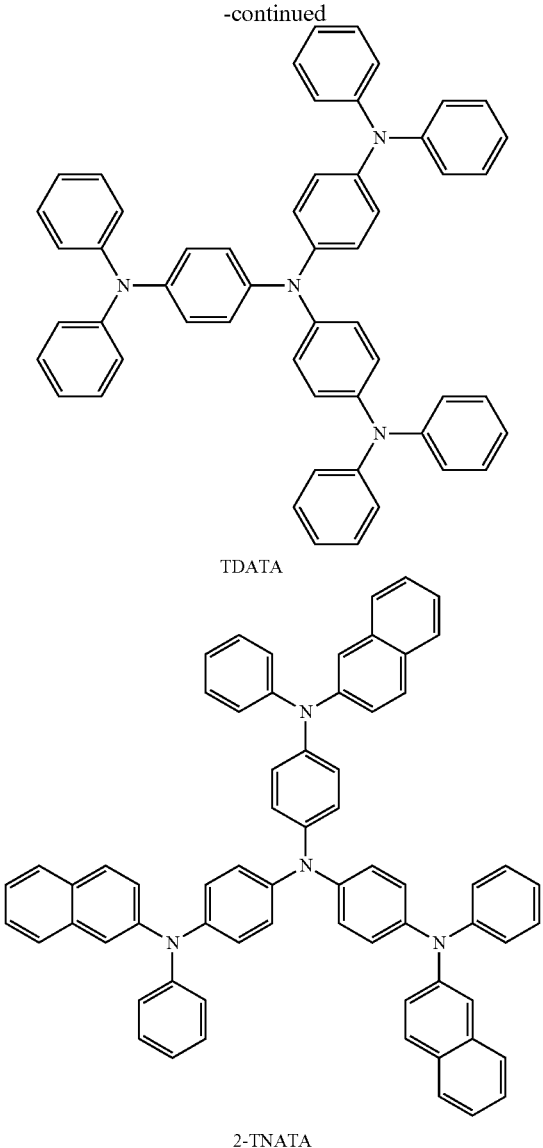

TDATA

2-TNATA

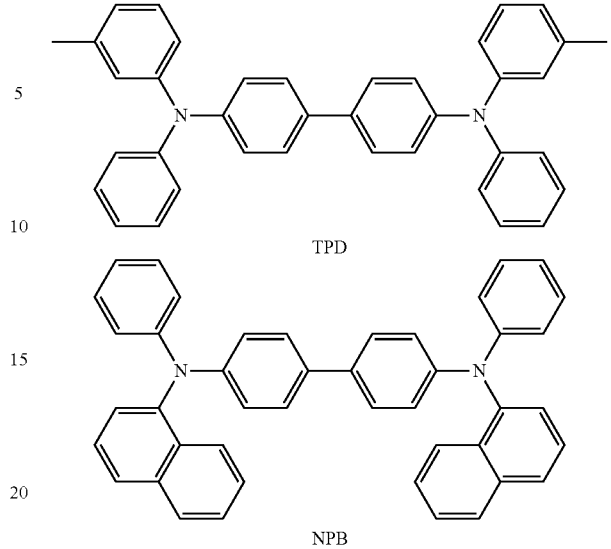

TPD

NPB

The thickness of the HTL may be from about 50 Å to about 2000 Å, and in some embodiments, may be from about 100 Å to about 1500 Å. In one embodiment, when the thickness of the HTL is within these ranges, the HTL has good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 50 Å to about 10,000 Å, and in some embodiments, may be from about 100 Å to about 1,000 Å. In one embodiment, when the thickness of the H-functional layer is within these ranges, the H-functional layer has good hole injection and transport capabilities without a substantial increase in driving voltage.

In some embodiments, at least one of the HIL, HTL, and H-functional layer may include at least one of a compound of Formula 300 below and a compound of Formula 350 below:

The thickness of the HIL may be about 100 Å to about 10000 Å, and in some embodiments, may be from about 100 Å to about 1000 Å. In one embodiment, when the thickness of the HIL is within these ranges, the HIL has good hole injecting ability without a substantial increase in driving voltage.

Then, an HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary depending on the material that is used to form the HTL.

The HTL may be formed of any suitable hole-transporting materials. Non-limiting examples of suitable HTL forming materials are carbazole derivatives (such as N-phenylcarbazole or polyvinylcarbazole), N,N'-bis(3-methylphenyl)-N,N'-diphenyl-[1,1-biphenyl]-4,4'-diamine (TPD), 4,4',4''-tris (N-carbazolyl)triphenylamine (TCTA), and N,N'-di(1-naphthyl)-N,N'-diphenylbenzidine (NPB).

Formula 300

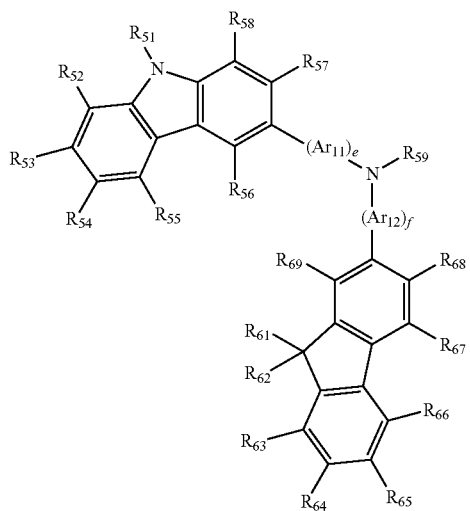

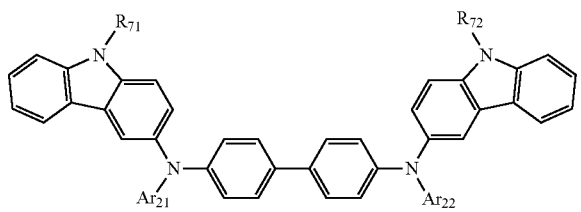

Formula 350

In Formulae 300 and 350, $Ar_{11}$, $Ar_{12}$, $Ar_2$, and $Ar_{22}$ may be each independently a substituted or unsubstituted $C_5$-$C_{60}$ arylene group.

In Formula 300, e and f may be each independently an integer from 0 to 5, for example, may be 0, 1, or 2. For example, e may be 1, and f may be 0, but not limited thereto.

In Formulae 300 and 350 above, $R_{51}$ to $R_{58}$, $R_{61}$ to $R_{69}$, and $R_{71}$ and $R_{72}$ may be each independently a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group or a $C_1$-$C_{10}$ alkoxy group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{109}$ may be one of a phenyl group, a naphthyl group, an anthryl group, a biphenyl group, a pyridyl group; or a phenyl group, a naphthyl group, an anthryl group, a biphenyl group, or a pyridyl group, each substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment, the compound of Formula 300 may be a compound represented by Formula 300A below:

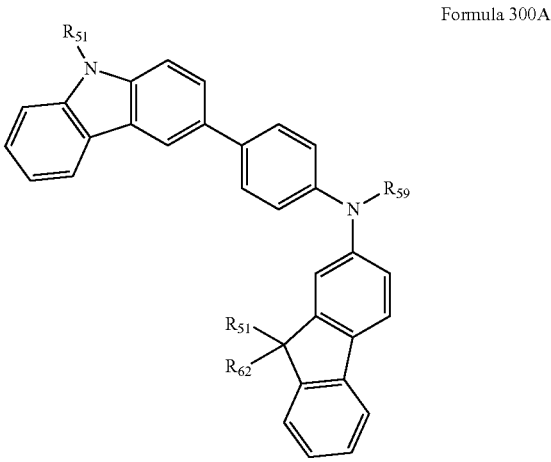

Formula 300A

In Formula 300A, $R_{51}$, $R_{61}$, $R_{62}$, and $R_{59}$ may be as defined above. In some embodiments, at least one of the HIL, HTL, and H-functional layer may include at least one of the compounds represented by Formulae 301 to 320 below:

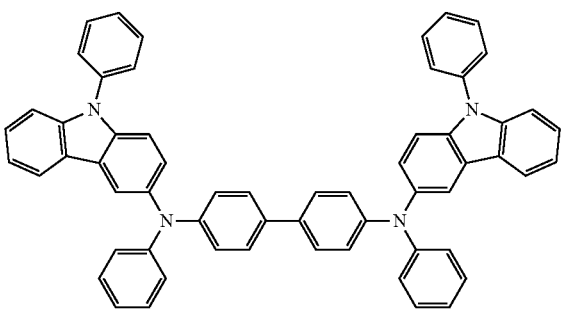

301

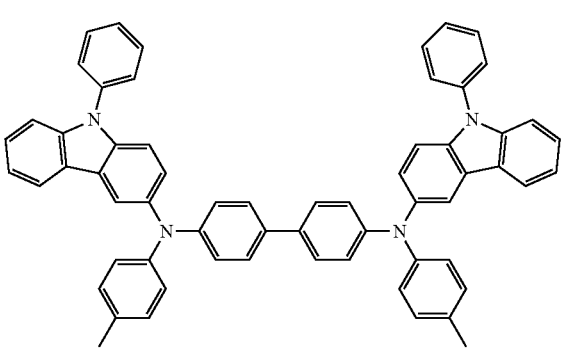

302

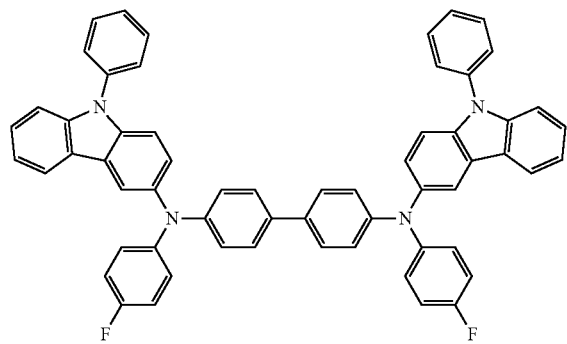
303
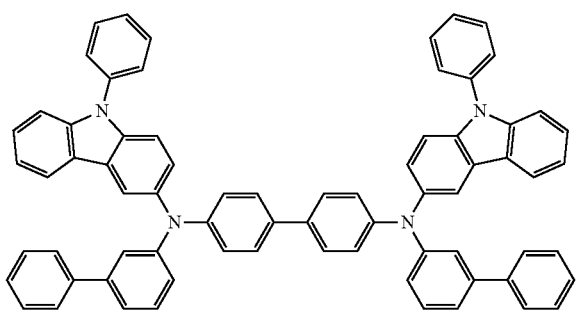
307
304
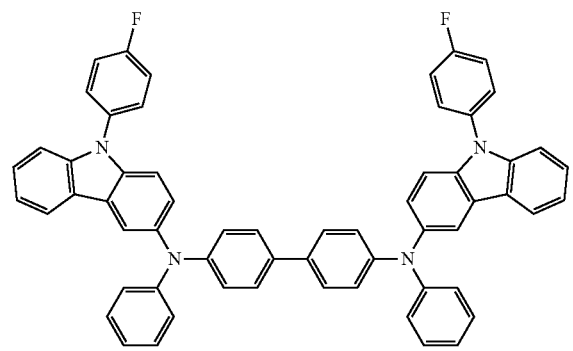
308
305
306
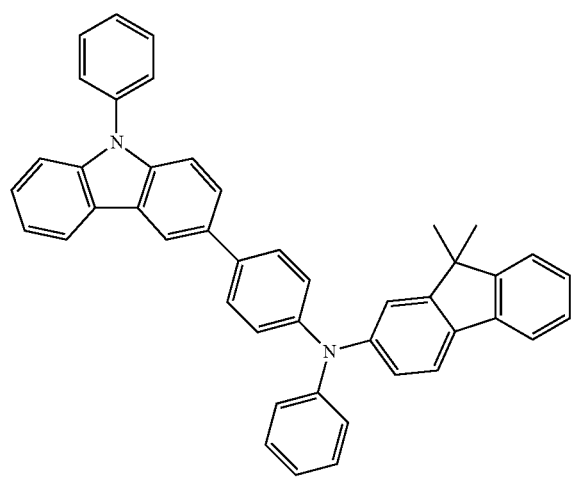
309

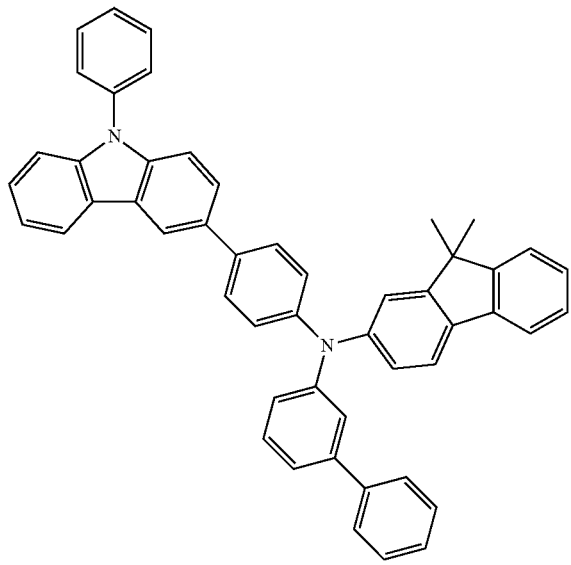
310
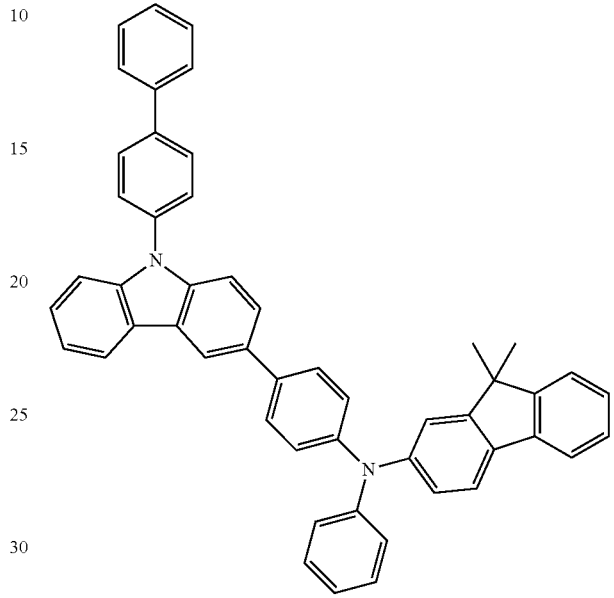
312
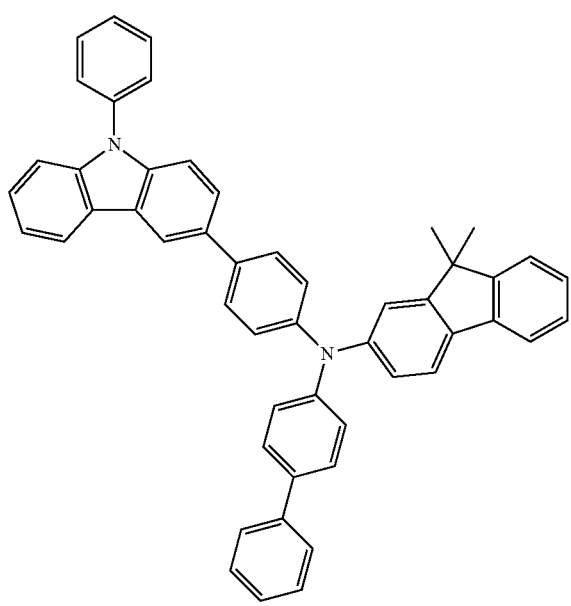
311
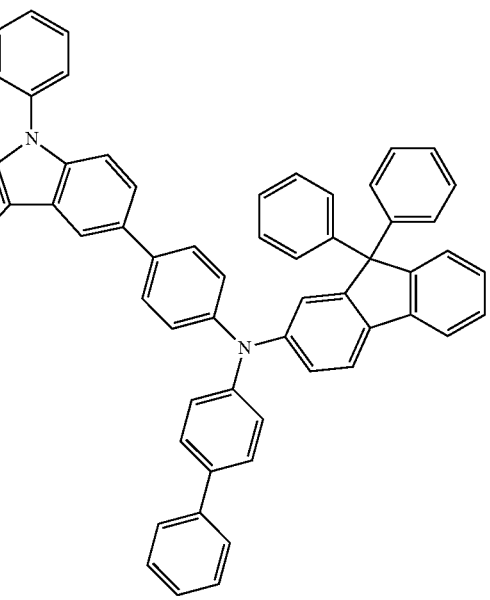
313

-continued
314
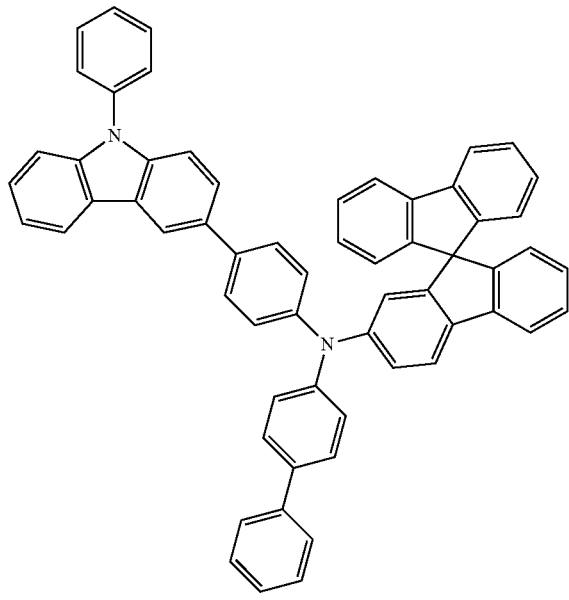
315
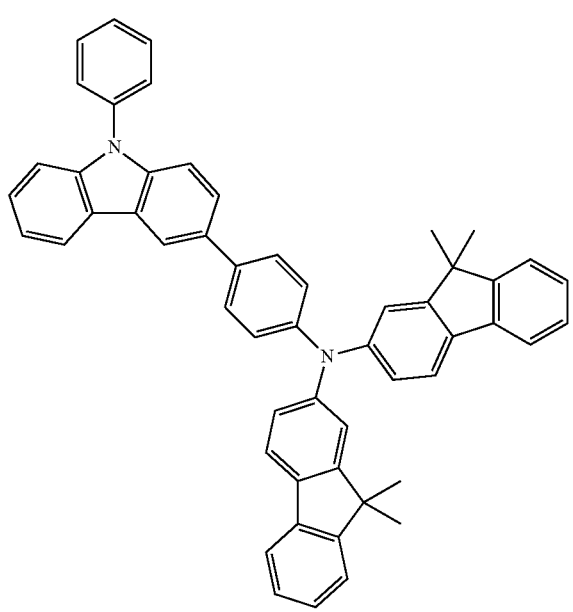
-continued
316
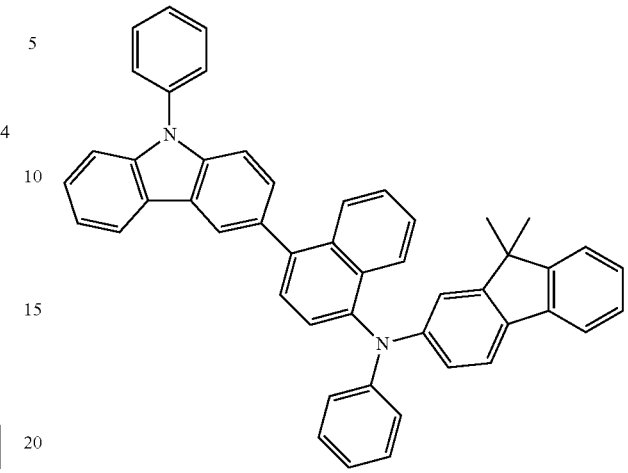
317
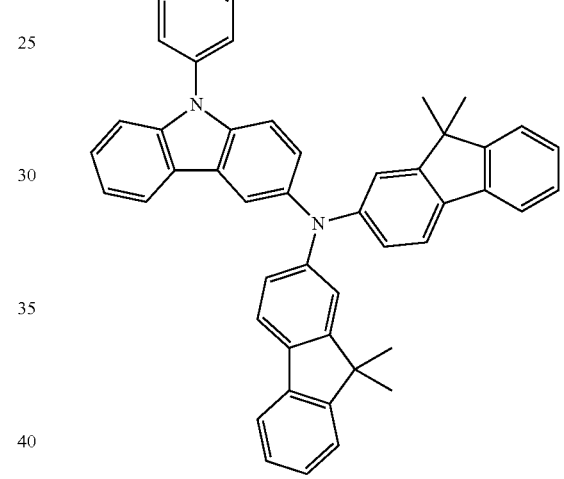
318
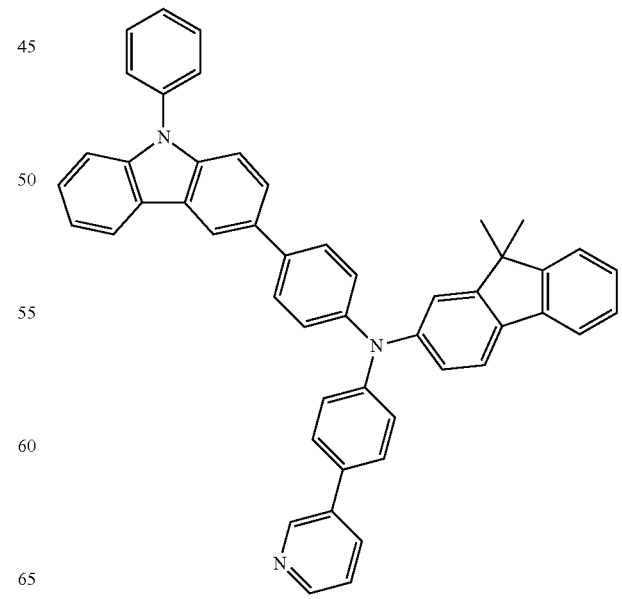

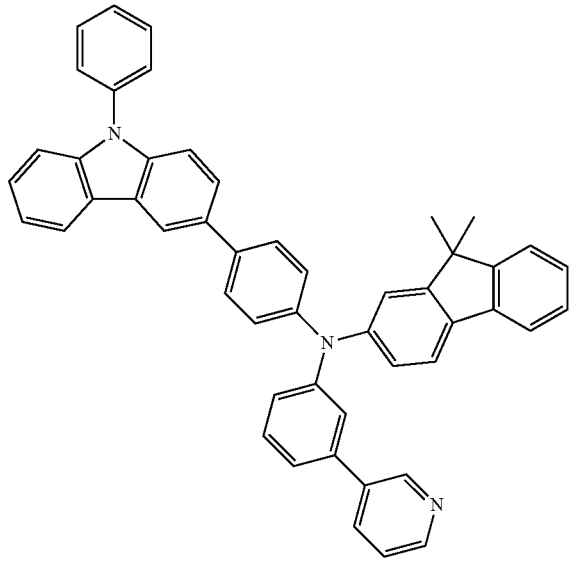
319

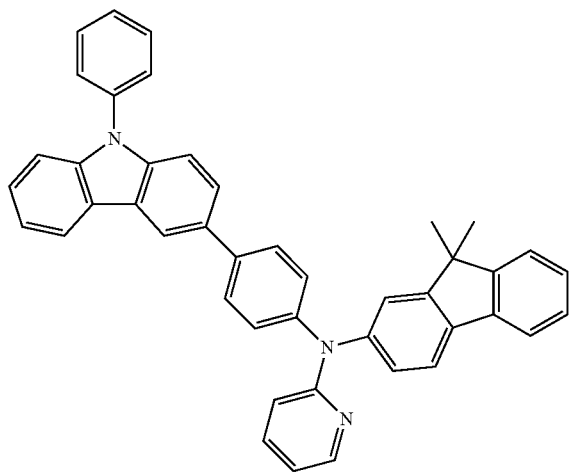
320

At least one of the HIL, HTL, and H-functional layer may further include a charge-generating material for improved layer conductivity, in addition to a suitable hole injecting material, hole transport material, and/or material having both hole injection and hole transport capabilities as described above.

The charge-generating material may be, for example, a p-dopant. The p-dopant may be one of quinone derivatives, metal oxides, or compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), or the like; metal oxides such as tungsten oxide, molybdenum oxide, or the like; and cyano-containing compounds such as Compound 200 below.

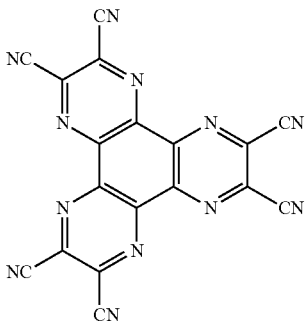
Compound 200

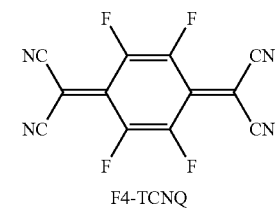
F4-TCNQ

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The buffer layer may include any suitable hole injecting material or hole transporting material. In some other embodiments, the buffer layer may include the same material as one of the materials included in the HIL, HTL, and H-functional layer that underly the buffer layer.

Then, an EML may be formed on the HTL, H-functional layer, or buffer layer by vacuum deposition, spin coating, casting, Langmuir-Blodgett (LB) deposition, or the like. When the EML is formed using vacuum deposition or spin coating, the deposition and coating conditions may be similar to those for the formation of the HIL, though the conditions for deposition and coating may vary depending on the material that is used to form the EML.

The EML may be formed using the compound of Formula 1 above, or any of a variety of suitable hosts or dopants. Dopants that may be used to form the EML may include either a suitable fluorescent dopant or a suitable phosphorescent dopant.

Non-limiting examples of the suitable host are $Alq_3$, 4,4'-N,N'-dicarbazole-biphenyl (CBP), poly(n-vinylcarbazole) (PVK), 9,10-di(naphthalene-2-yl)anthracene (DNA), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

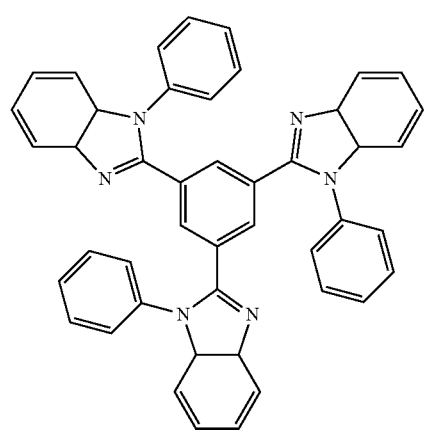
TPBI
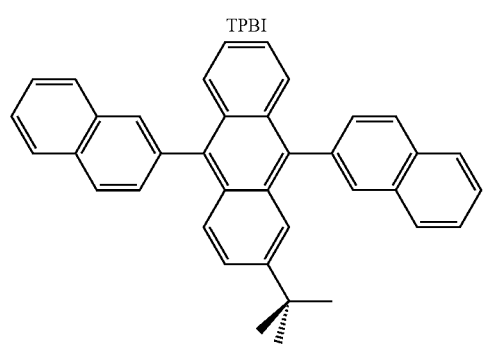
TBADN
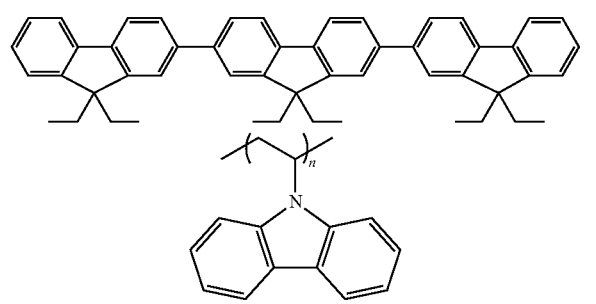
PVK
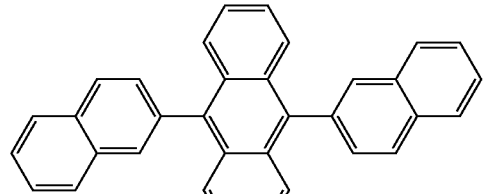
ADN
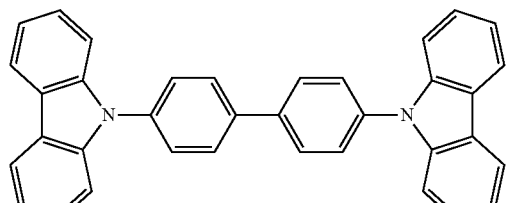
CBP
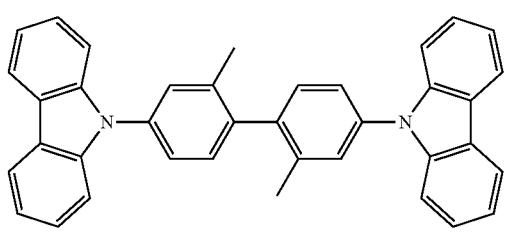
dmCBP
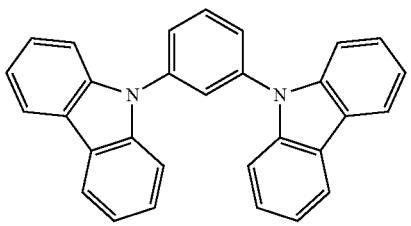
501
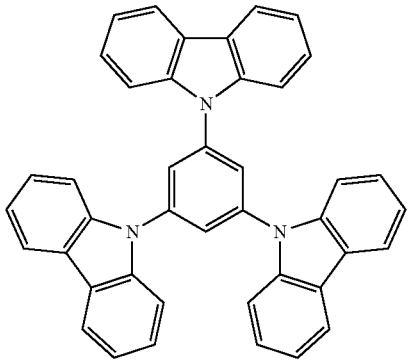
502
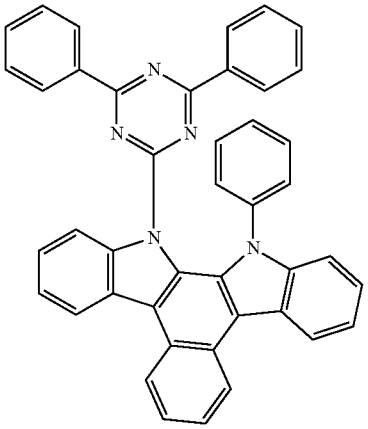
503

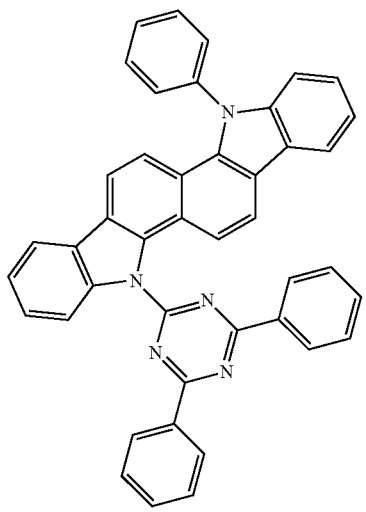

504

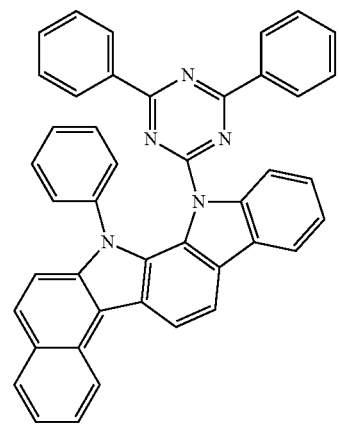

505

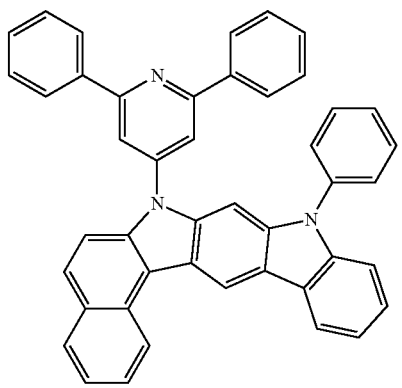

506

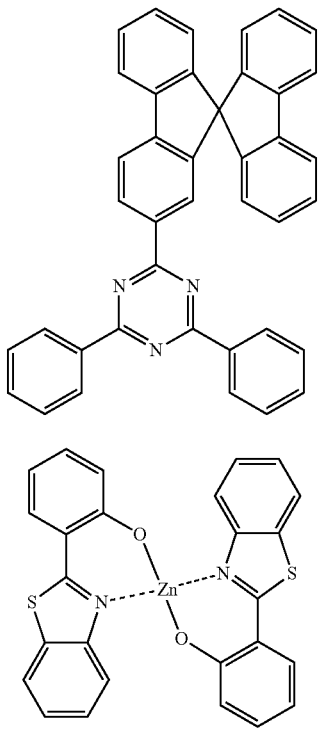

507

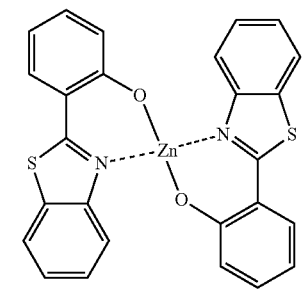

508

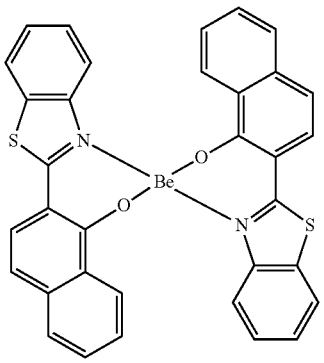

509

In some embodiments, an anthracene-based compound represented by Formula 400 below may be used as the host.

Formula 400>

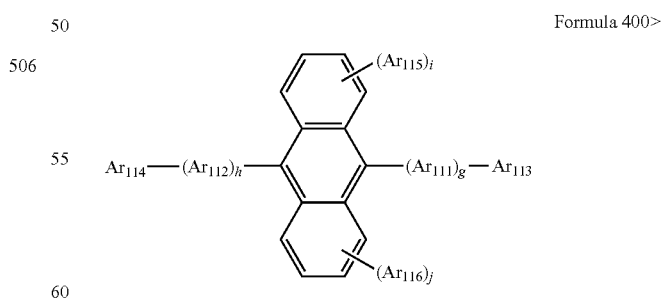

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_5$-$C_{60}$ aryl group; and g, h, l, and j are each independently an integer from 0 to 4.

In some embodiments, $Ar_{111}$ and $Ar_{112}$ in Formula 400 may be each independently a phenylene group; a naphthylene group; a phenanthrenylene group; a pyrenylene group; or a phenylene group, a naphthylene group, a phenanthrenylene group, a fluorenyl group, or a pyrenylene group, each substituted with at least one of a phenyl group, a naphthyl group, and an anthryl group.

In Formula 400 above, g, h, l, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; or a phenyl group, a naphthyl group, an anthryl group, a pyrenyl group, a phenanthrenyl group, or a fluorenyl group, each substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; or

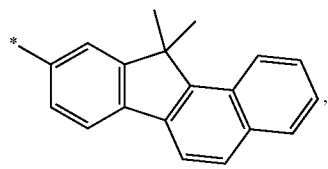 [SMILES: *c1ccc2c(c1)C(C)(C)c1c-2ccc2ccccc12]

, but are not limited thereto.

For example, the anthracene-based compound of Formula 400 above may be one of the compounds represented by the following formulae, but is not limited thereto:

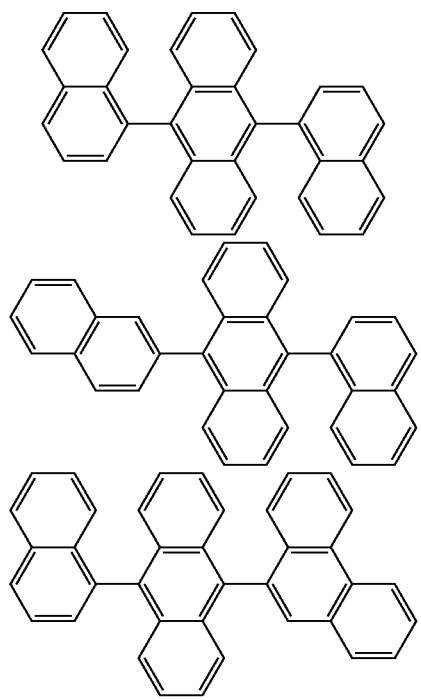

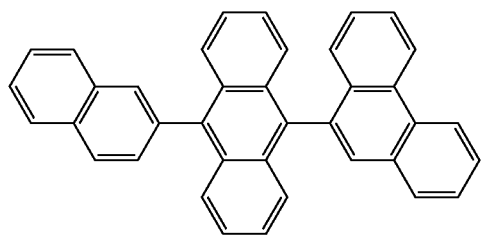

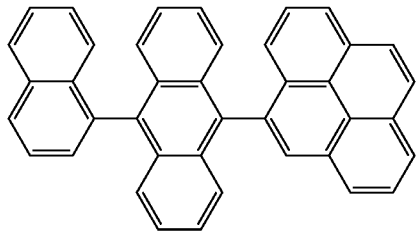

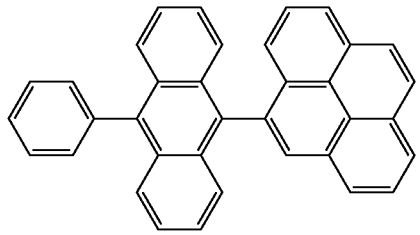

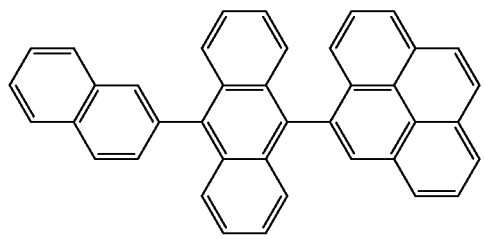

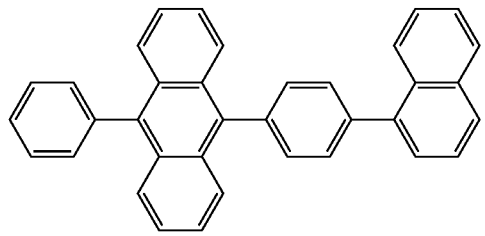

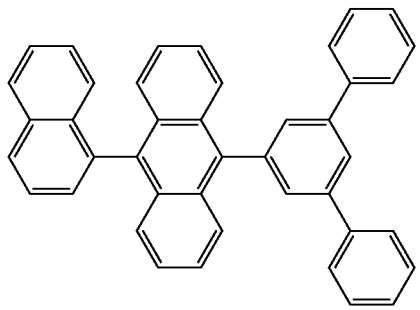

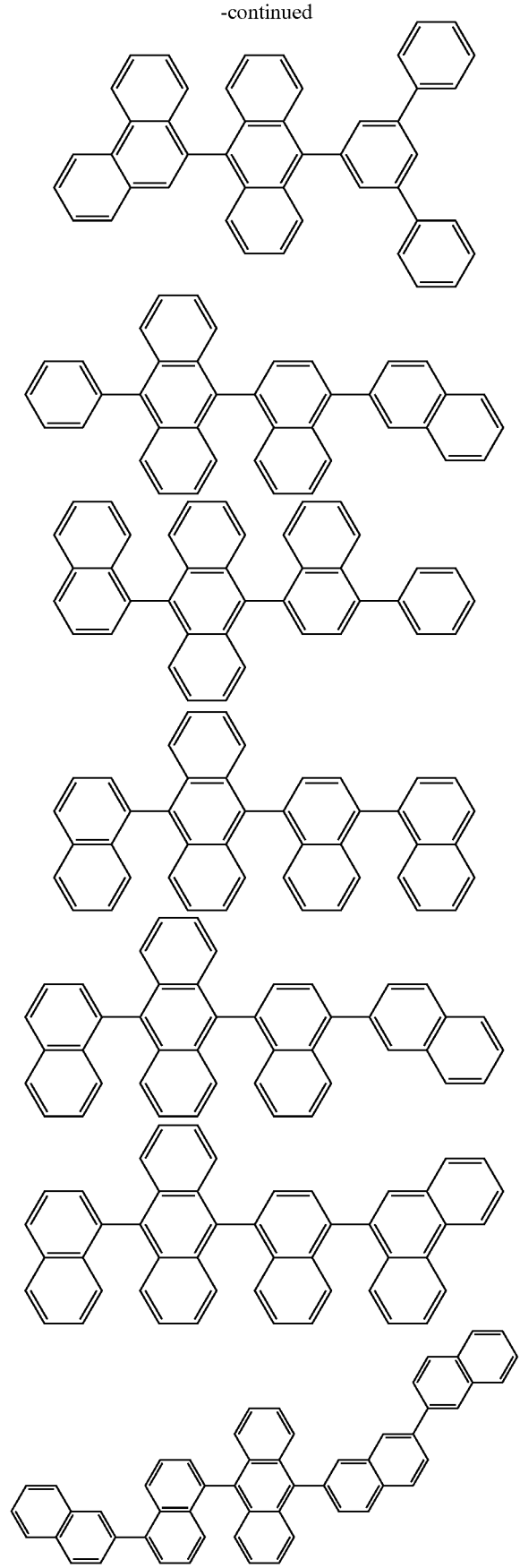
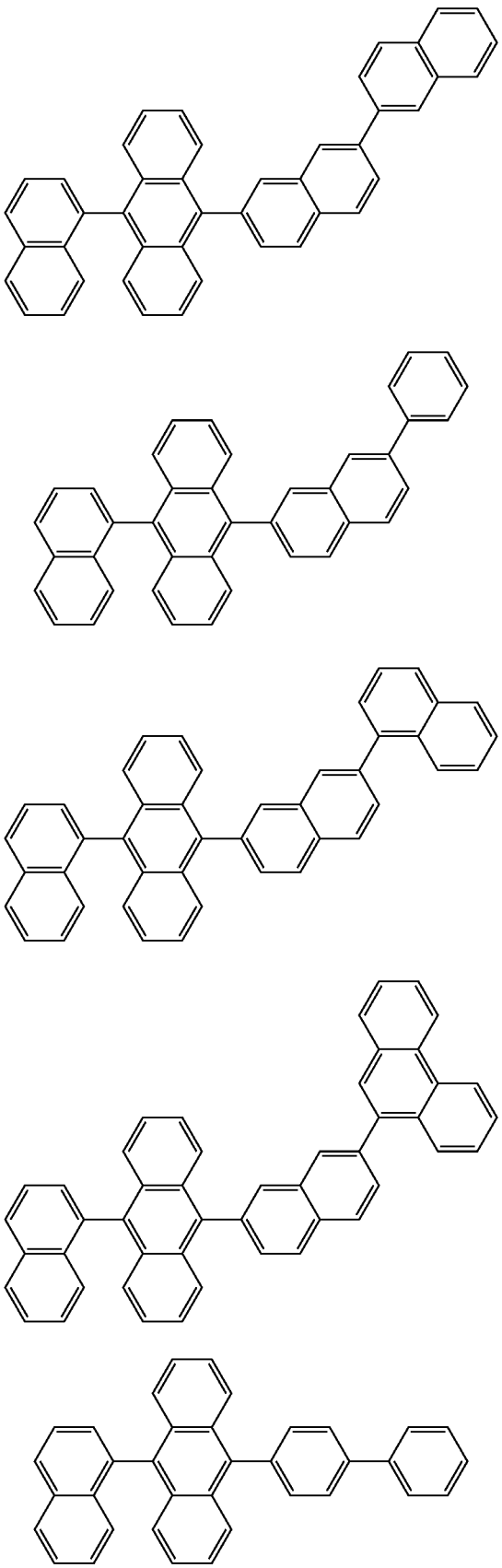

-continued
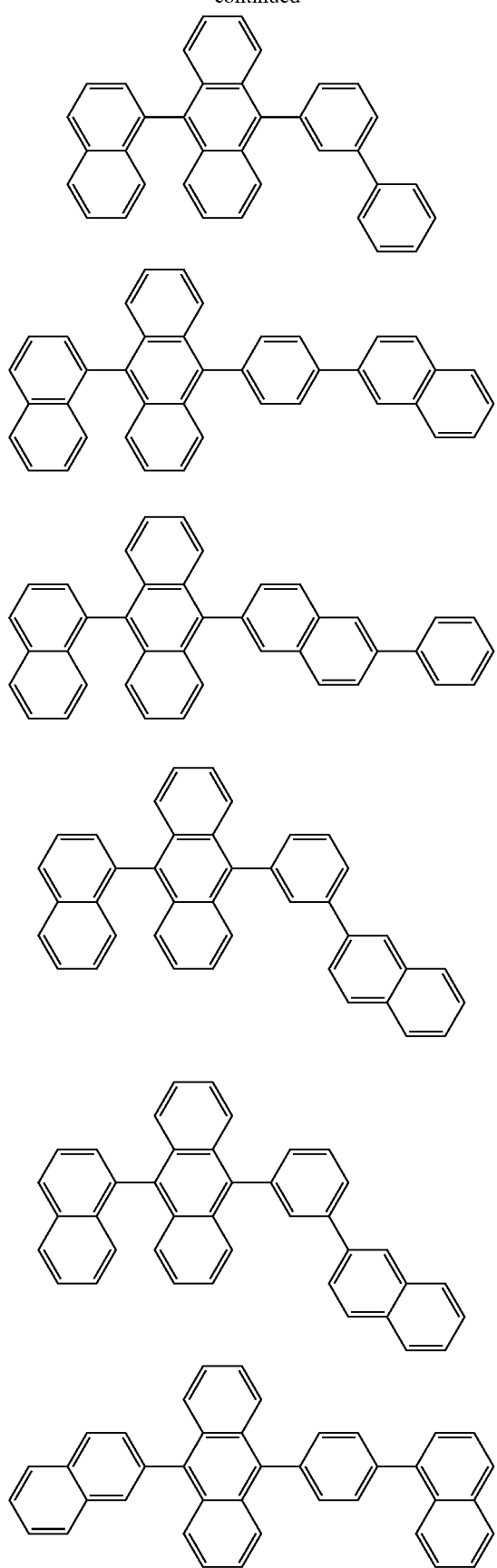
-continued
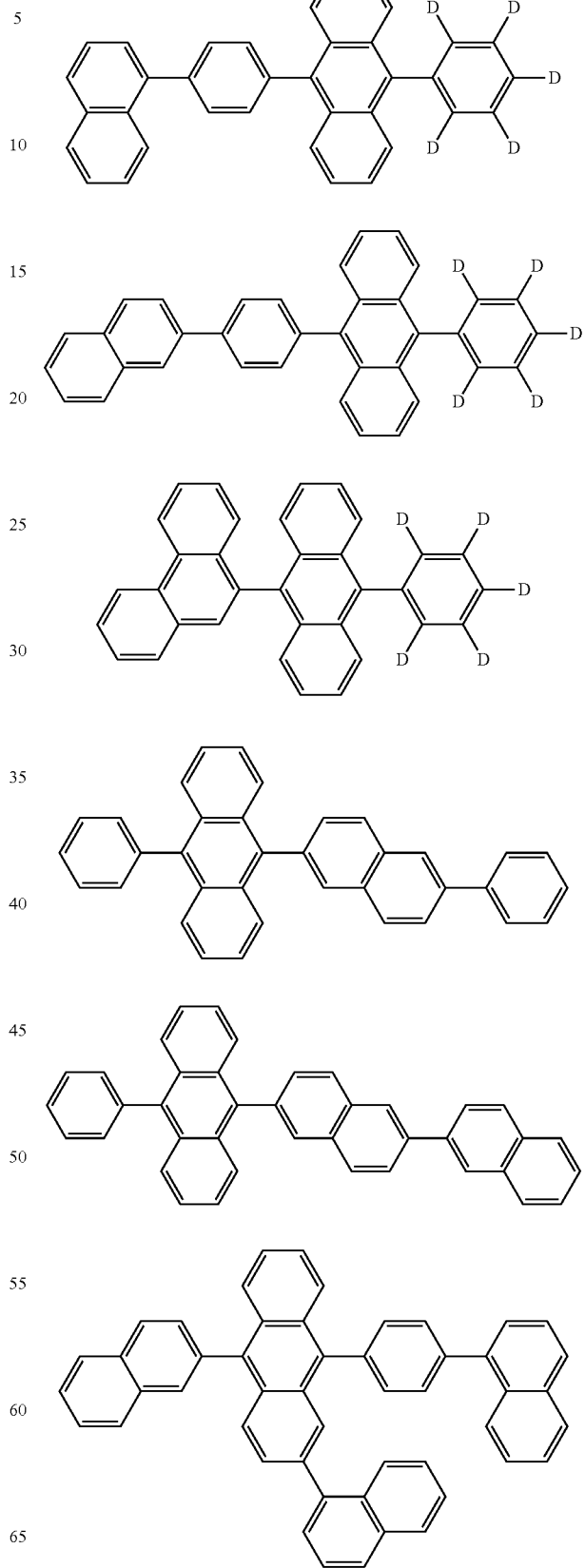

-continued

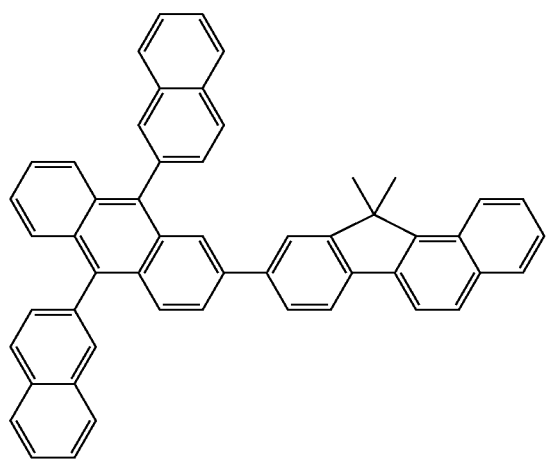

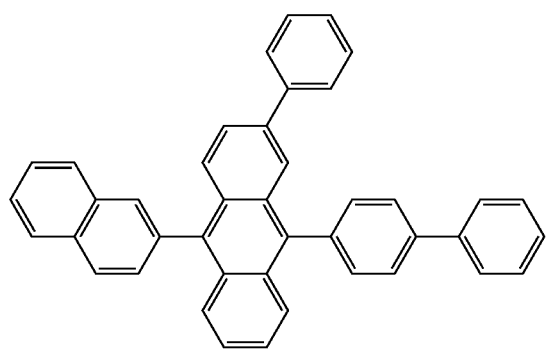

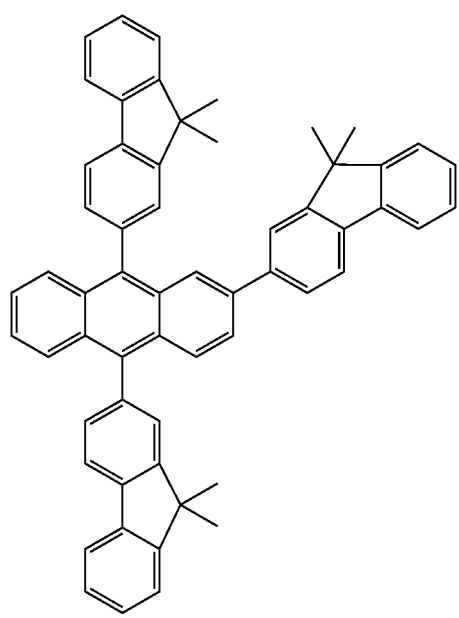

-continued

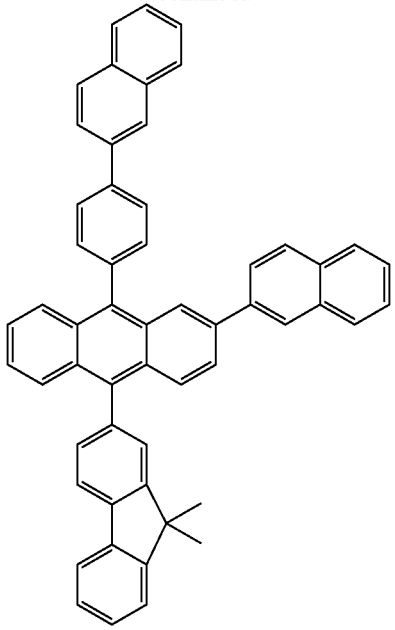

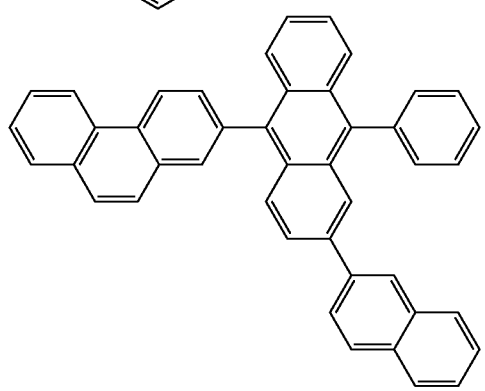

In some embodiments, an anthracene-based compound represented by Formula 401 below may be used as the host.

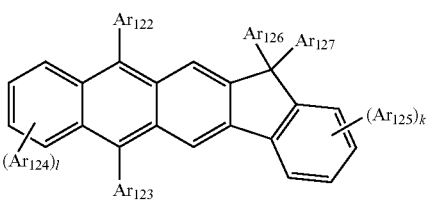

Formula 401

$Ar_{122}$ to $Ar_{125}$ in Formula 401 above may be defined as described above in conjunction with $Ar_{113}$ of Formula 400, and thus detailed descriptions thereof will not be provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

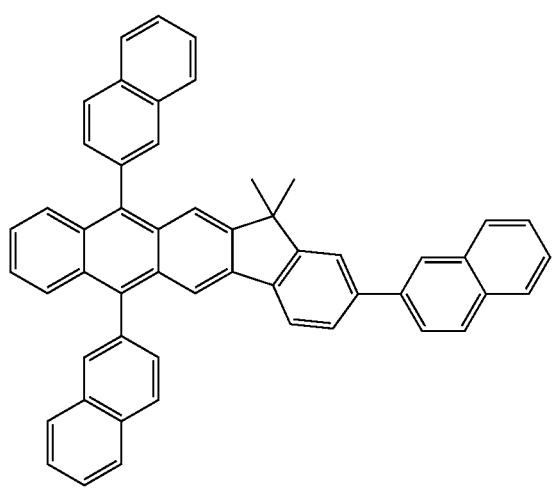

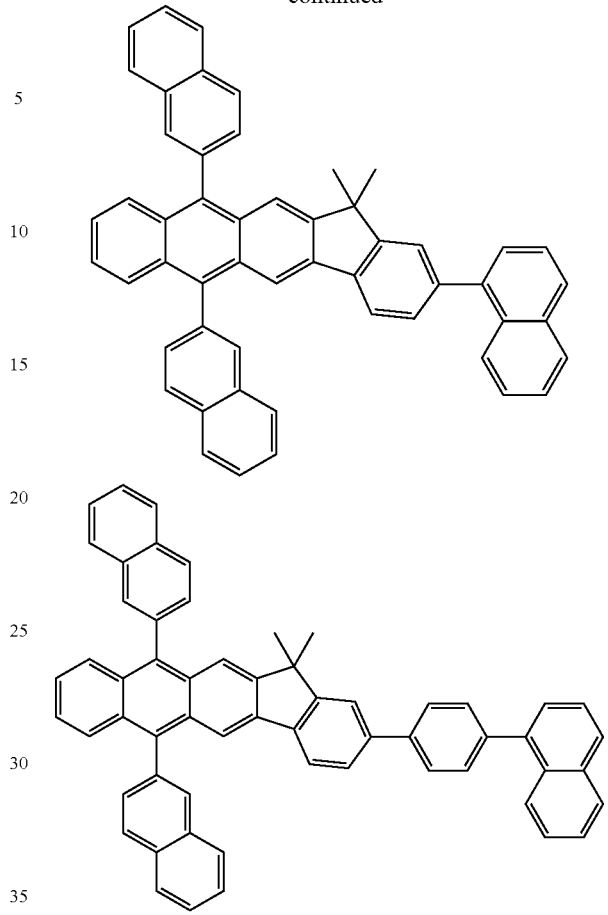

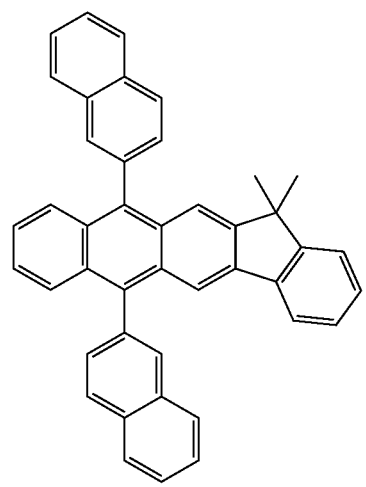

When the organic light-emitting device is a full color organic light-emitting device, the emission layer may be patterned into a red emission layer (red EML), a green emission layer (green EML), and a blue emission layer (blue EML).

At least one of the red EML, the green EML, and the blue EML may include a dopant below (ppy=phenylpyridine).

Non-limiting examples of the blue dopant are compounds represented by the following formulae.

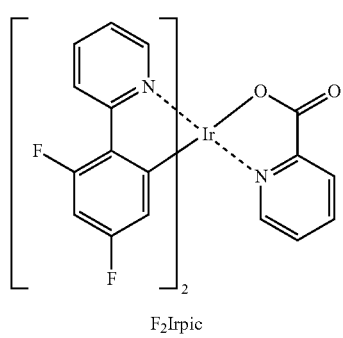

F₂Irpic

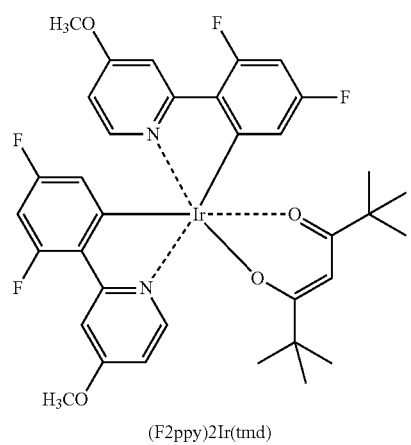

(F2ppy)2Ir(tmd)

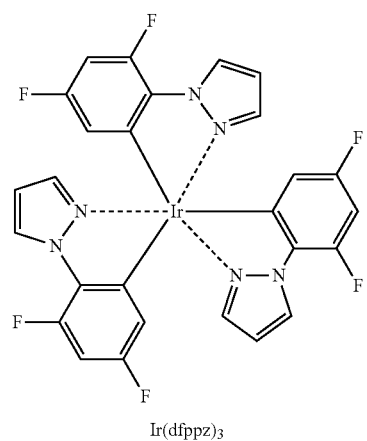

Ir(dfppz)₃

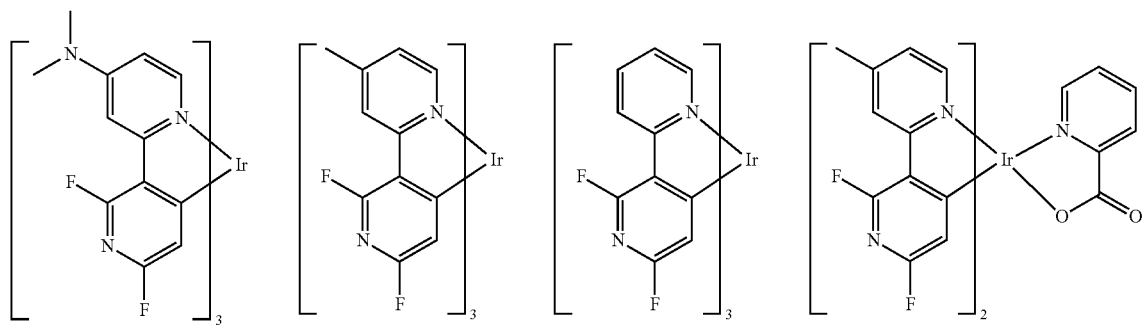
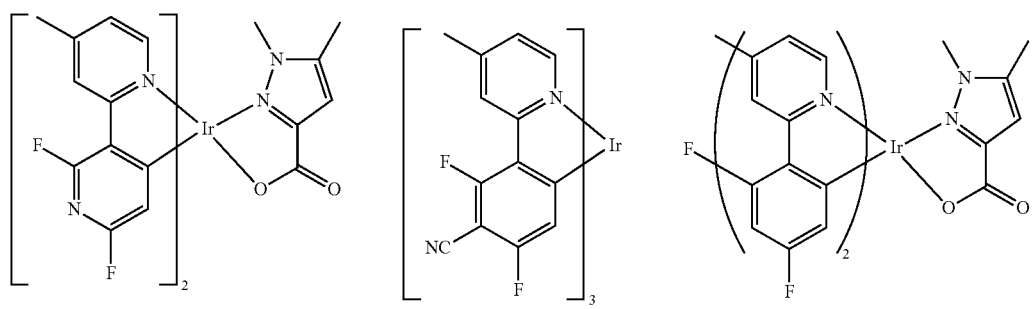
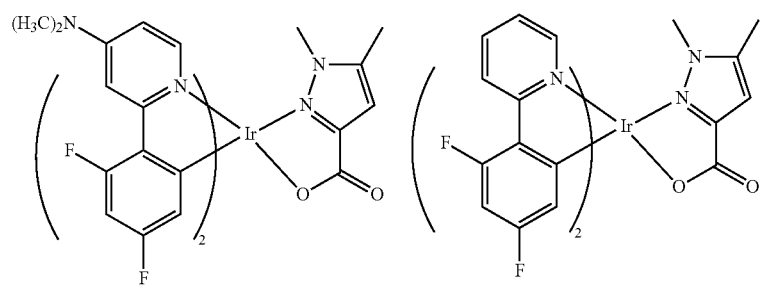
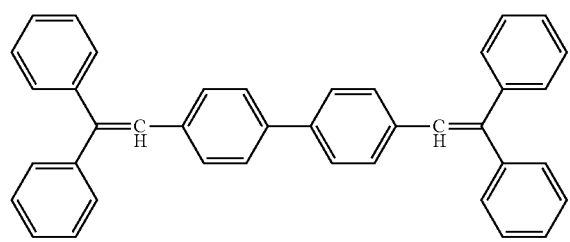
DPVBi
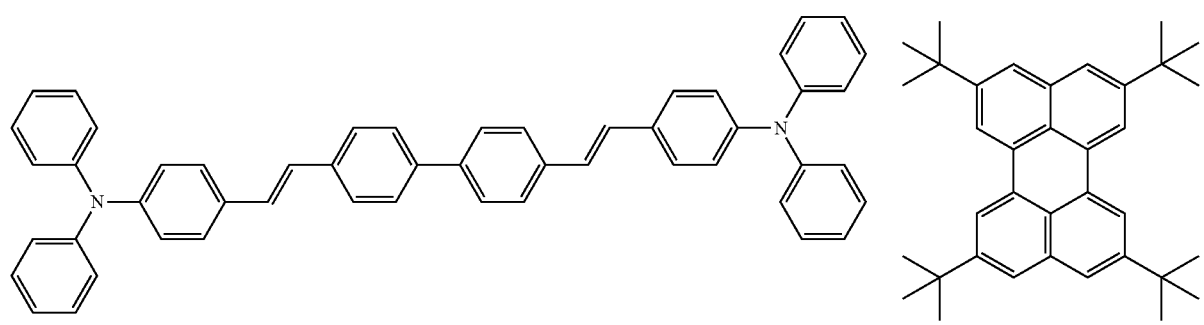
DPAVBi
TBPe

Non-limiting examples of the red dopant are compounds represented by the following formulae.
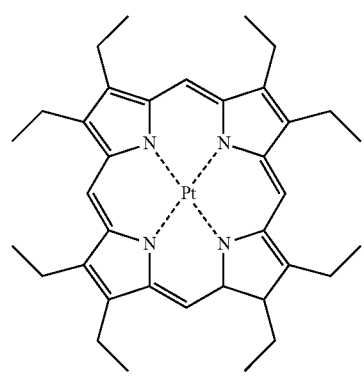
PtOEP
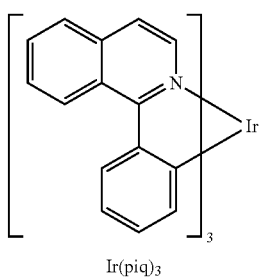
Ir(piq)₃
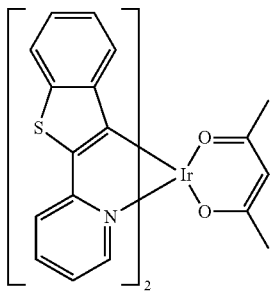
Btp₂Ir(acac)
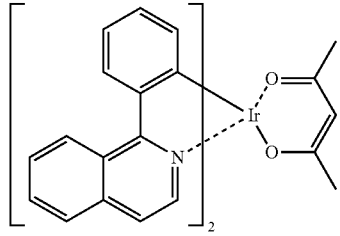
Ir(pq)₂(acac)
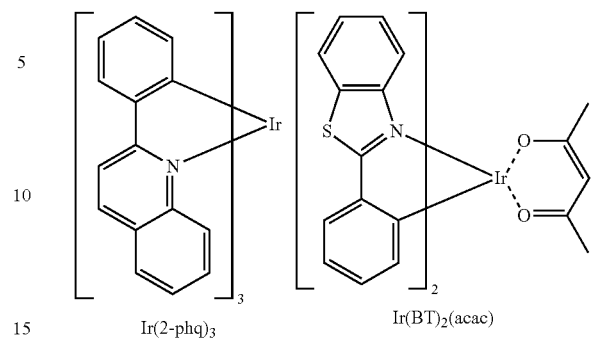
Ir(2-phq)₃
Ir(BT)₂(acac)
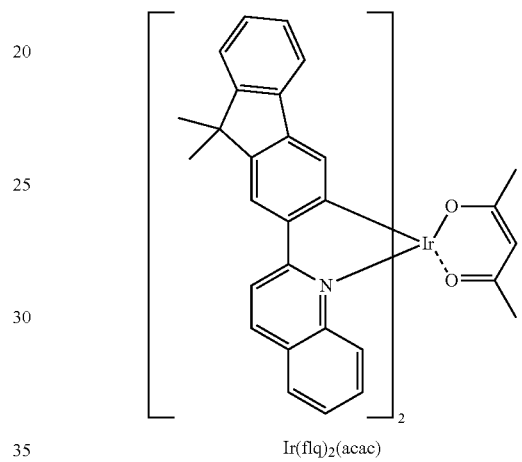
Ir(flq)₂(acac)
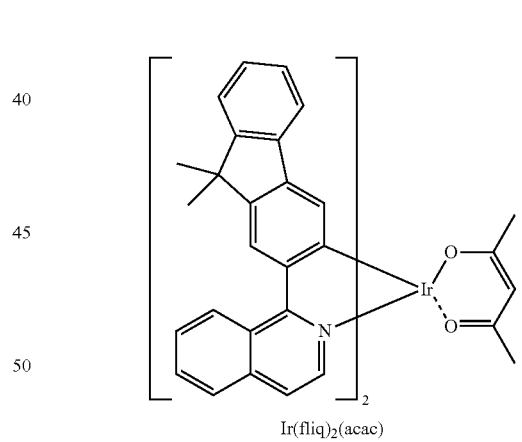
Ir(fliq)₂(acac)
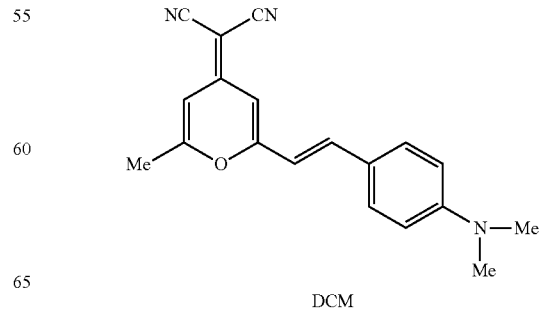
DCM

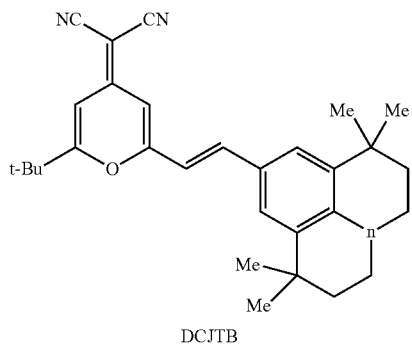
DCJTB
Non-limiting examples of the green dopant are compounds represented by the following formulae.
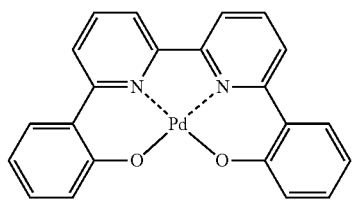
D1
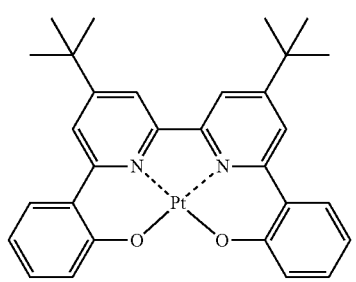
D2
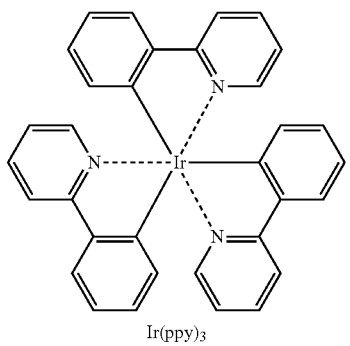
Ir(ppy)₃
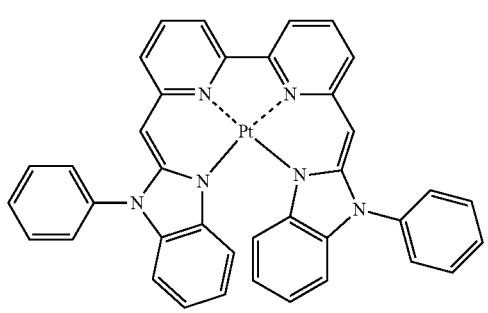
D3
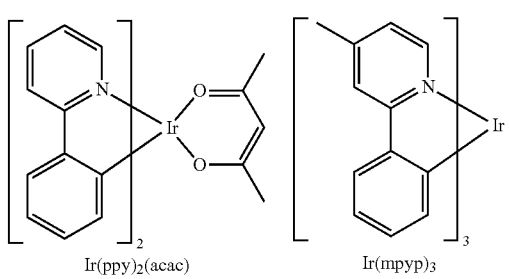
Ir(ppy)₂(acac)     Ir(mpyp)₃
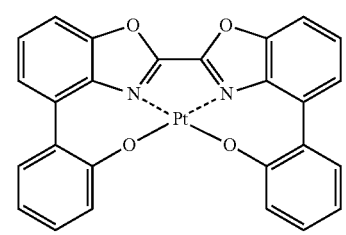
D4
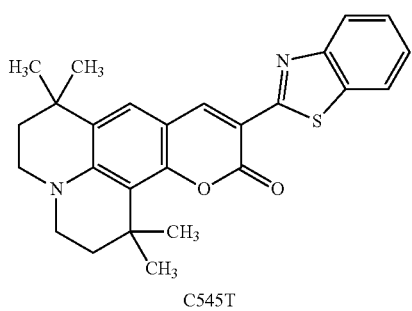
C545T
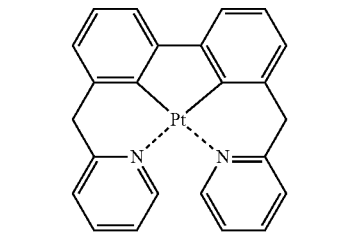
D5
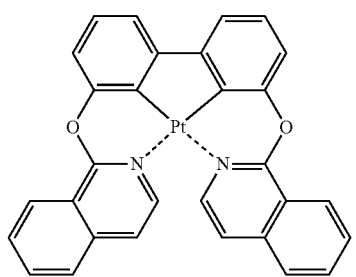
D6
Non-limiting examples of the dopant that may be used in the EML are Pd complexes or Pt complexes represented by the following formulae.

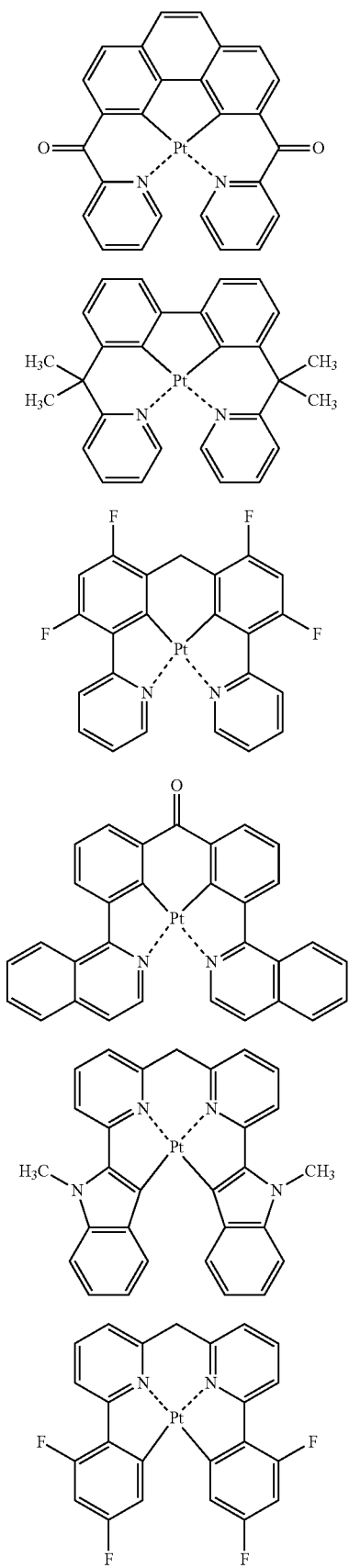
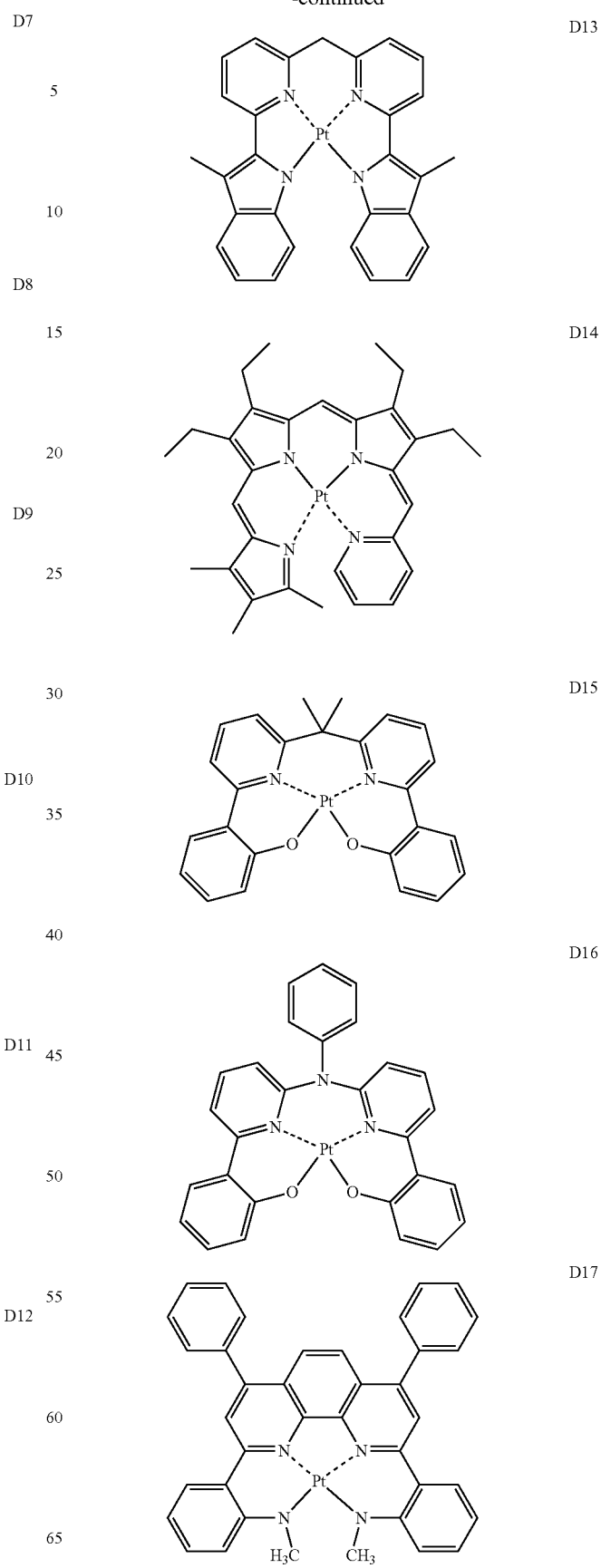

D18 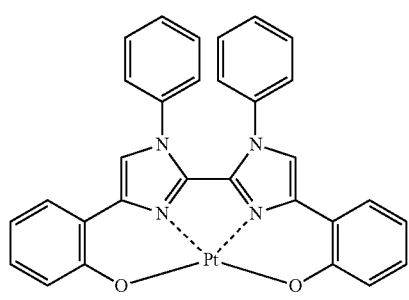
D19 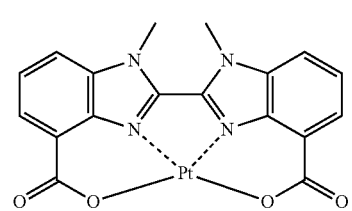
D20 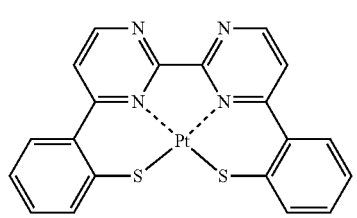
D21 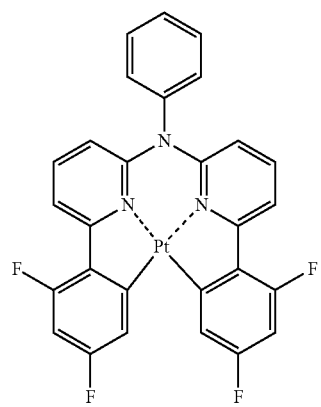
D22 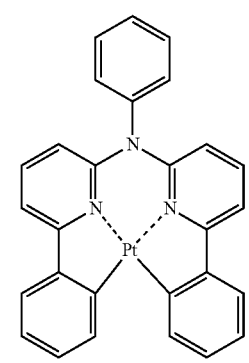
D23 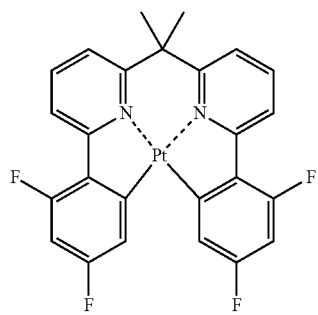
D24 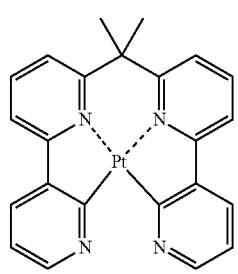
D25 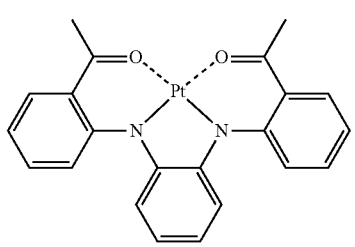
D26 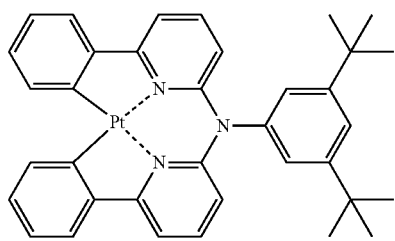
D27 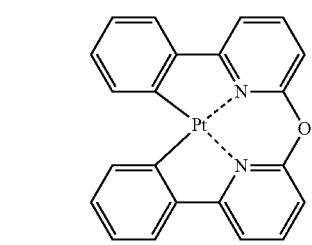
D28 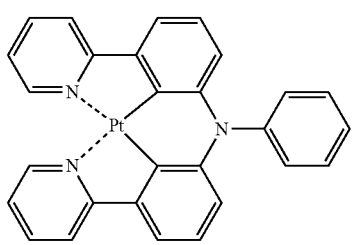

D29 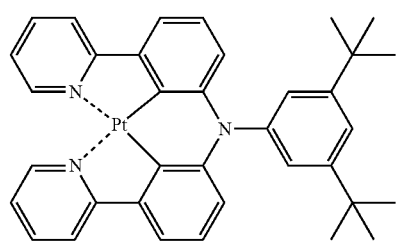
D30 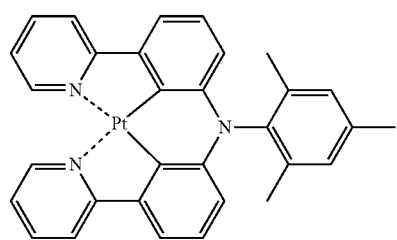
D31 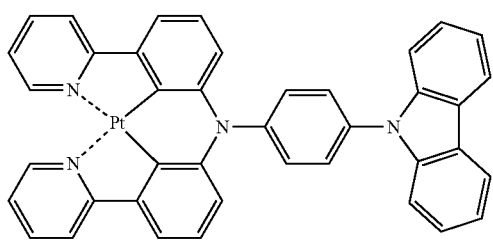
D32 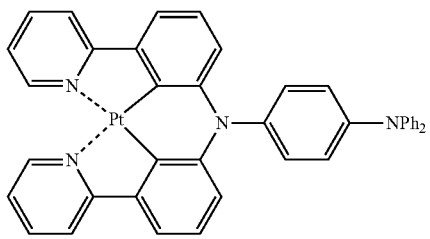
D33 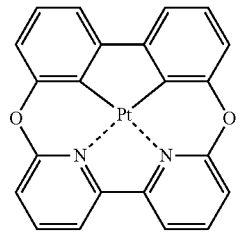
D34 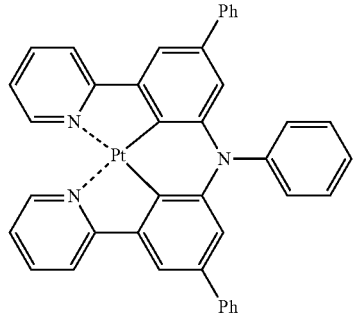
D35 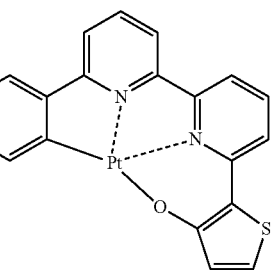
D36 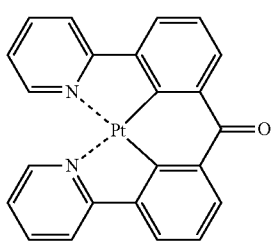
D37 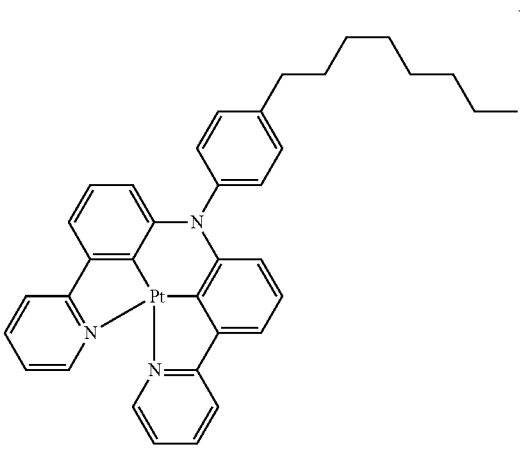
D38 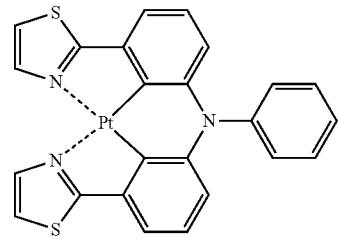
D39 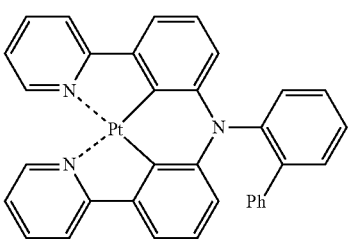

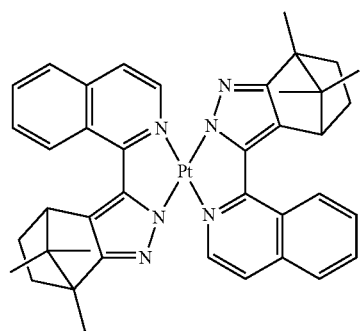 D40
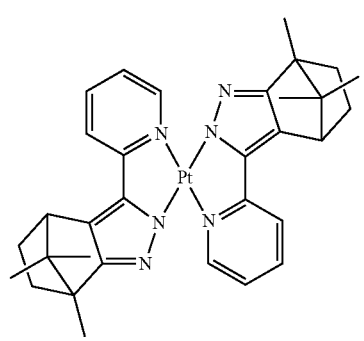 D41
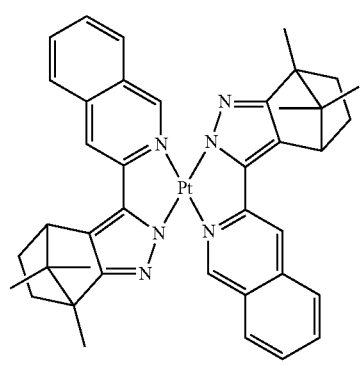 D42
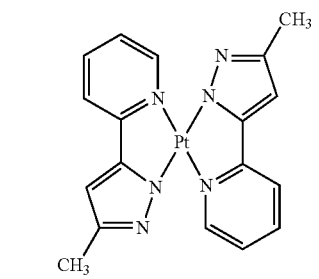 D43
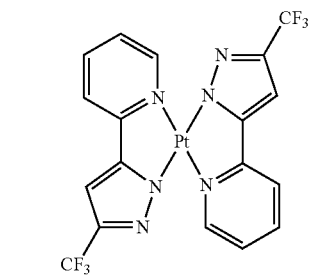 D44
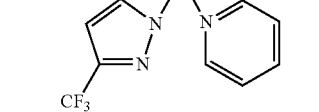 D45
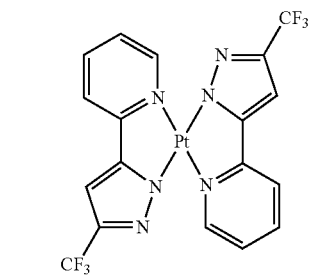 D46
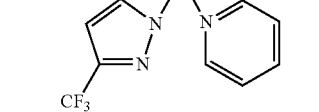 D47
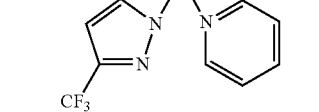 D48
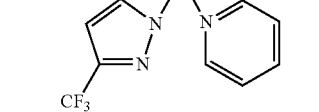 D49

-continued

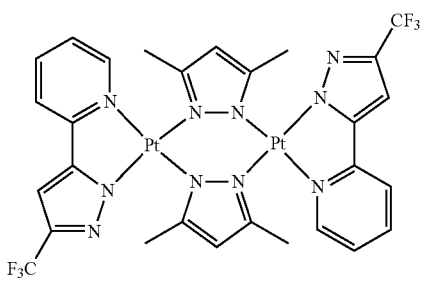

D50

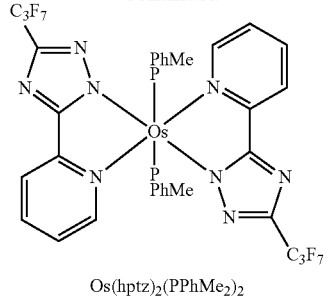

Os(hptz)₂(PPhMe₂)₂

Non-limiting examples of the dopant that may be used in the EML are Os-complexes represented by the following formulae.

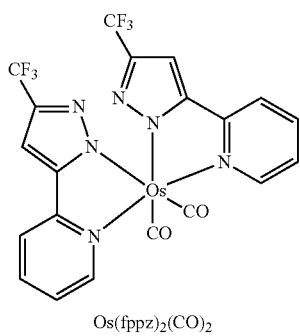

Os(fppz)₂(CO)₂

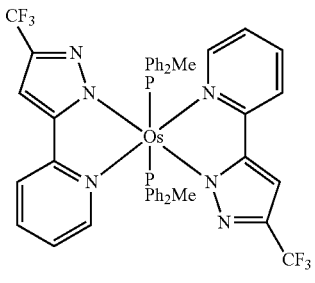

Os(fppz)₂(PPh₂Me)₂

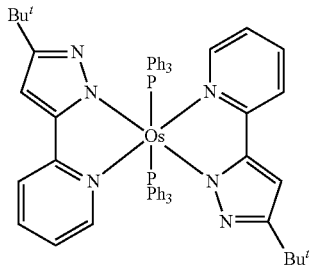

Os(bppz)₂(PPh₃)₂

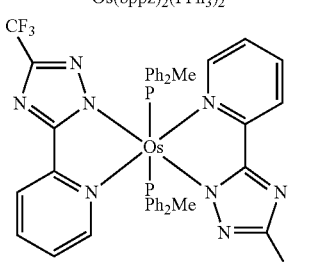

Os(fptz)₂(PPh₂Me)₂

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. In one embodiment, when the thickness of the EML is within these ranges, the EML has good light emitting ability without a substantial increase in driving voltage.

Then, an ETL may be formed on the EML by vacuum deposition, spin coating, casting, or the like.

When the ETL is formed using vacuum deposition or spin coating, the deposition and coating conditions may be similar to those for the formation of the HIL, though the deposition and coating conditions may vary depending on the compound that is used to form the ETL.

A material for forming the ETL may be a suitable material that may stably transport electrons injected from an electron injecting electrode (cathode).

Non-limiting examples of materials for forming the ETL are a quinoline derivative (such as tris(8-quinolinorate) aluminum (Alq₃)), TAZ, BAlq, beryllium bis(benzoquino-lin-10-olate (Bebq₂), 9,10-di(naphthalene-2-yl)anthracene (ADN), BCP, Compound 201, and Compound 202.

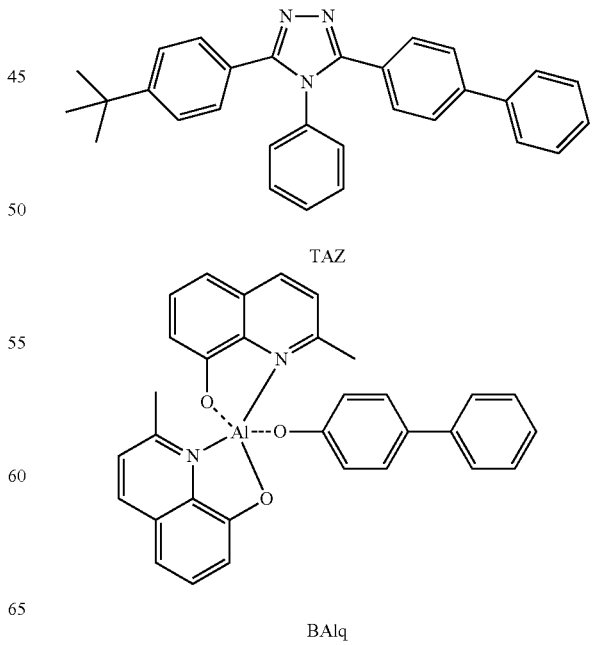

TAZ

BAlq

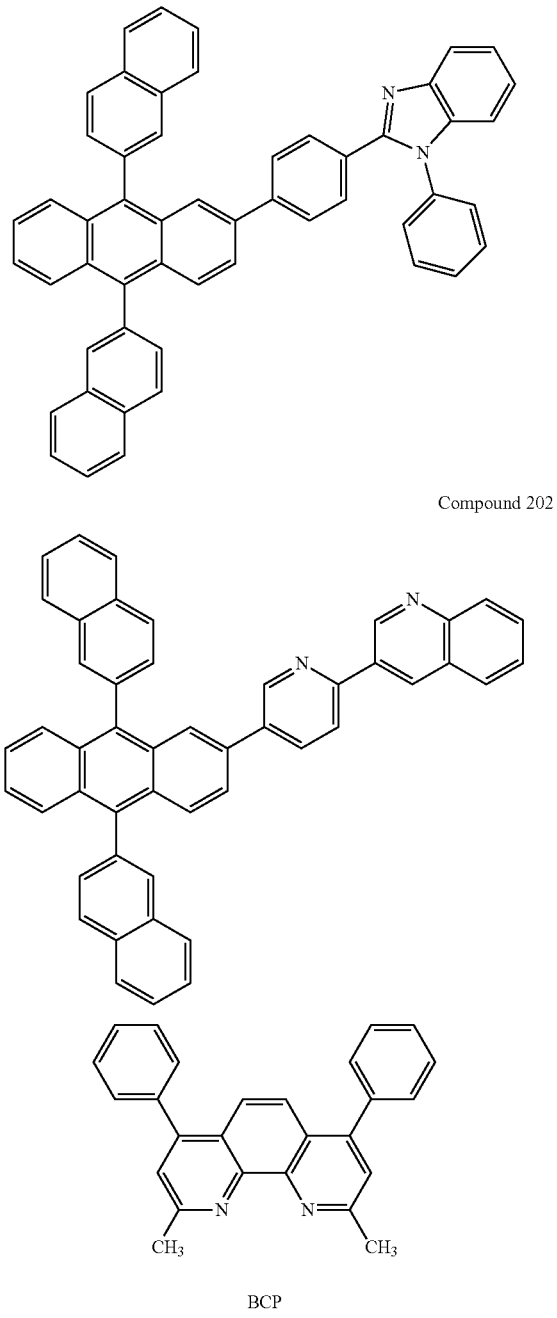

Compound 201

Compound 202

BCP

Compound 203

The thickness of the ETL may be from about 100 Å to about 1,000 Å, and in some embodiments, may be from about 150 Å to about 500 Å. In one embodiment, when the thickness of the ETL is within these ranges, the ETL has satisfactory electron transporting ability without a substantial increase in driving voltage.

In some embodiments the ETL may further include a metal-containing material, in addition to any suitable electron-transporting organic compound.

The metal-containing material may include a lithium (Li) complex. Non-limiting examples of the Li complex are lithium quinolate (LiQ) and Compound 203 below:

Then, an EIL, which facilitates injection of electrons from the cathode, may be formed on the ETL. Any suitable electron-injecting material may be used to form the EIL.

Non-limiting examples of suitable materials for forming the EIL are LiF, NaCl, CsF, $Li_2O$, and BaO. The deposition and coating conditions for forming the EIL may be similar to those for the formation of the HIL, though the deposition and coating conditions may vary depending on the material that is used to form the EIL.

The thickness of the EIL may be from about 1 Å to about 100 Å, and in some embodiments, may be from about 3 Å to about 90 Å. In one embodiment, when the thickness of the EIL is within these ranges, the EIL has satisfactory electron injection ability without a substantial increase in driving voltage.

Finally, the second electrode is disposed on the organic layer. The second electrode may be a cathode that is an electron injection electrode. A suitable material for forming the second electrode may be a metal, an alloy, an electroconductive compound, which has a low work function, or a mixture thereof. In this regard, the second electrode may be formed of lithium (Li), magnesium (Mg), aluminum (Al), aluminum-lithium (Al—Li), calcium (Ca), magnesium-indium (Mg—In), magnesium-silver (Mg—Ag), or the like, and may be formed as a thin film transmission electrode. In some embodiments, to manufacture a top-emission light-emitting device, the transmission electrode may be formed of indium tin oxide (ITO) or indium zinc oxide (IZO).

Although the organic light-emitting device of the drawing is described above, embodiments of the present invention are not limited thereto.

When a phosphorescent dopant is used in the EML, a hole blocking layer (HBL) may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary depending on the material that is used to form the HBL. Any suitable hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

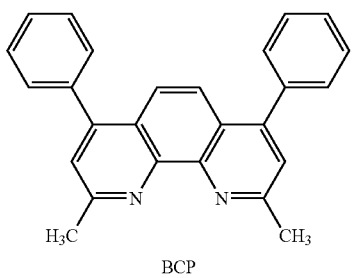
BCP

The thickness of the HBL may be from about 20 Å to about 1000 Å, and in some embodiments, may be from about 30 Å to about 300 Å. In one embodiment, when the thickness of the HBL is within these ranges, the HBL has improved hole blocking ability without a substantial increase in driving voltage.

According to embodiments of the present invention, the organic light-emitting device may be included in various flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may be formed of the compound of Formula 1 by using a deposition method or may be formed using a wet method of coating a solution of the compound of Formula 1.

Hereinafter, the present invention will be described in more detail with reference to the following synthesis examples and other examples. However, these examples are for illustrative purposes only and are not intended to limit the scope of the present invention.

EXAMPLES

Synthesis Example 1

Synthesis of Compound 18

Synthesis of Intermediate 18-1

[Reaction Scheme 18-1]

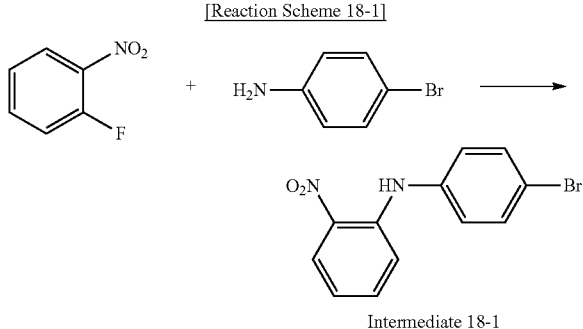

Intermediate 18-1

5.00 g (35.44 mmol) of 1-fluoro-2-nitrobenzene, 12.19 g (70.87 mmol) of 4-bromoaniline, 2.57 g (44.30 mmol) of potassium fluoride (KF) were mixed together and reacted at about 170° C. for about 72 hours. After completion of the reaction, the reaction product was extracted with dichloromethane and then washed with distilled water. The resulting product was purified by column chromatography using methyl chloroform (MC) as an eluent, and then recrystallized using methanol to obtain 3.10 g of Compound 18-1 (Yield: 30%).

$^1$H NMR (400 MHz, CDCl3) δ 9.37 (s, 1H), 8.19 (d, J=8.6 Hz, 1H), 7.51 (d, J=8.6 Hz, 2H), 7.37 (t, J=7.8 Hz, 1H), 7.24~7.14 (m, 3H), 6.80 (t, J=7.4 Hz, 1H).

$^{13}$C NMR (CDCl3, 100 MHz) δ 142.36, 137.93, 135.73, 133.50, 132.80, 126.74, 125.70, 118.40, 118.04, 115.94.

MALDI-TOF MS: calcd for C12H9BrN2O2 291.98. found 290.37.

Synthesis of Intermediate 18-2

[Reaction Scheme 18-2]

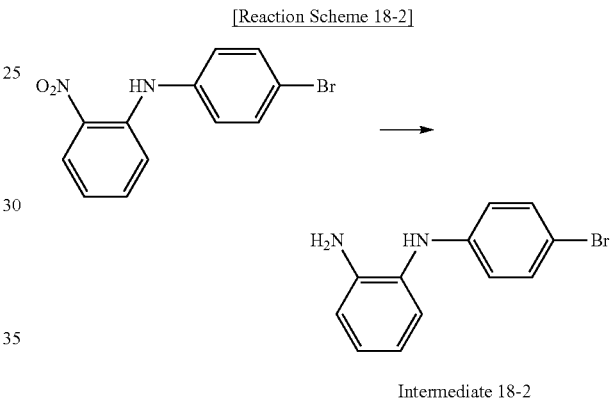

Intermediate 18-2

2.00 g (6.85 mmol) of Intermediate 18-1 and 7.73 g (34.25 mmol) of SnCl$_2$ (stannous chloride) were dissolved in ethanol and refluxed for about 24 hours. The reaction product was neutralized with an aqueous sodium bicarbonate solution, and extracted with ethyl acetate. The resulting product was purified by column chromatography using a 1:3 mixture of ethyl acetate and hexane as an eluent to obtain 1.78 g of Intermediate 18-2 (Yield: 99%).

$^1$H NMR (400 MHz, CDCl3) δ 7.26 (d, J=11.4 Hz, 2H), 7.08~7.01 (m, 2H), 6.80~6.73 (m, 2H), 6.58 (d, J=8.2 Hz, 2H), 5.16 (s, 1H), 3.71 (s, 2H).

$^{13}$C NMR (CDCl3, 100 MHz) δ 144.53, 142.12, 132.04, 127.70, 126.28, 125.26, 119.17, 116.62, 116.22, 110.95.

MALDI-TOF MS: calcd for C12H11BrN2 262.01. found 262.32.

Synthesis of Intermediate 18-3

[Reaction Scheme 18-3]

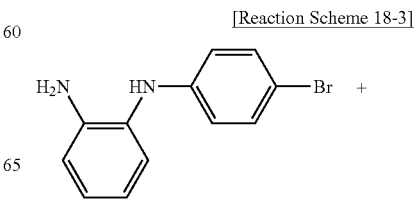

-continued

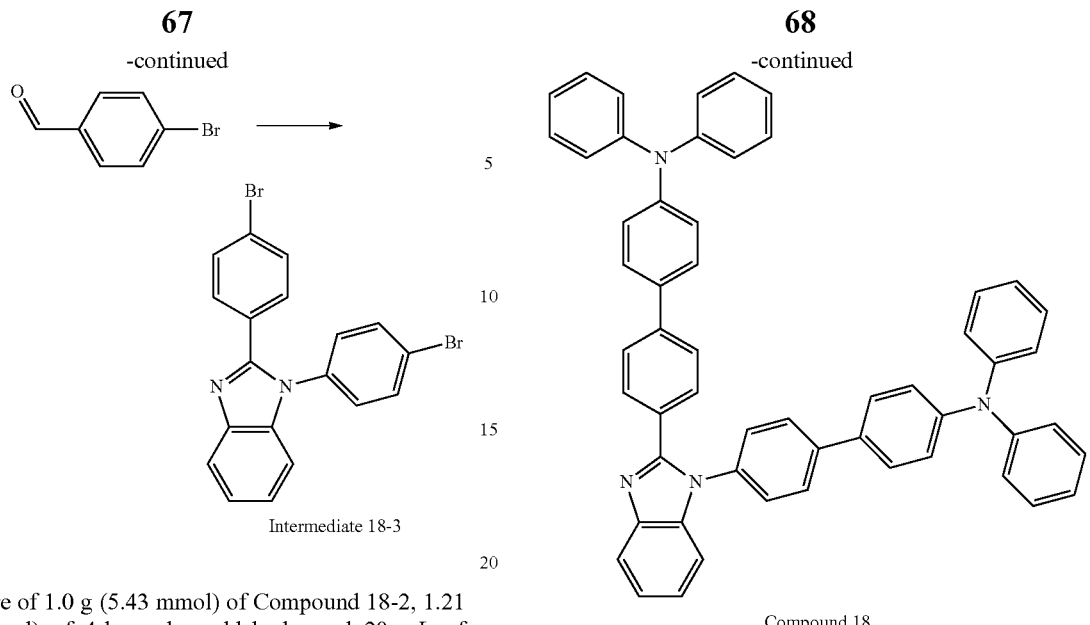

Intermediate 18-3

A mixture of 1.0 g (5.43 mmol) of Compound 18-2, 1.21 g (6.51 mmol) of 4-bromobenzaldehyde, and 20 mL of acetic acid was refluxed for about 12 hours. The reaction product was extracted with MC. An organic layer was washed with an aqueous sodium bicarbonate solution, and then purified by column chromatography using a 1:6 mixture of ethyl acetate and hexane as an eluent to obtain 1.11 g of Intermediate 18-3 (Yield: 47%).

$^1$H NMR (400 MHz, CDCl3) δ 7.86 (d, J=7.8 Hz, 1H), 7.63 (d, J=7.9 Hz, 2H), 7.43 (dd, J=8, 12 Hz, 4H), 7.34 (t, J=7 Hz, 1H), 7.32~7.16 (m, 4H).

$^{13}$C NMR (CDCl3, 100 MHz) δ 151.09, 142.95, 136.91, 135.78, 133.29, 131.74, 130.83, 128.87, 128.57, 124.29, 123.82, 123.40, 122.65, 120.08, 110.22.

MALDI-TOF MS: calcd for C19H12Br2N2 425.94. found 427.23.

Synthesis of Compound 18

-continued

Compound 18

0.85 g (2.00 mmol) of Intermediate 18-3, 0.70 g (2.00 mmol) of 4-(diphenylamino)phenylboroic acid, 0.12 g (0.10 mmol) of tetrakis(triphenylphosphine)palladium, and 2 M (20 ml) of an aqueous sodium carbonate solution were refluxed in a solvent of tetrahydrofuran (40 mL) and methanol (10 mL) for about 24 hours. The reaction product was extracted with MC, and then purified by column chromatography using a 1:1 mixture of MC and hexane as an eluent to obtain 0.65 g of Compound 18 (Yield: 74%).

$^1$H NMR (400 MHz, CDCl3) δ 7.89 (d, J=8.4 Hz, 1H), 7.70 (d, J=8.4 Hz, 2H), 7.66 (d, J=8.4 Hz, 2H), 7.52 (d, J=8.4, 2 Hz, 4H), 7.46 (d, J=8.4 Hz, 2H), 7.38 (d, J=8.4 Hz, 2H), 7.34~7.23 (m, 11H), 7.17~7.09 (m, 12H), 7.03 (q, J=8.4 Hz, 4H).

$^{13}$C NMR (CDCl3, 100 MHz) δ 152.19, 147.85, 147.65, 147.51, 147.48, 143.09, 141.40, 140.81, 137.32, 135.59, 133.67, 133.17, 129.83, 129.34, 129.28, 128.20, 127.78, 127.72, 127.63, 126.28, 124.61, 124.52, 123.62, 123.28, 123.21, 123.08, 122.99, 119.78, 110.46.

MALDI-TOF MS: calcd for C55H40N4 756.33 g/mol. found 756.77 g/mol. HRMS (FAB+)[M+H: C55H40N4]: calcd for 757.3331. found 757.3331.

Synthesis Example 2

Synthesis of Compound 20

Compound 20

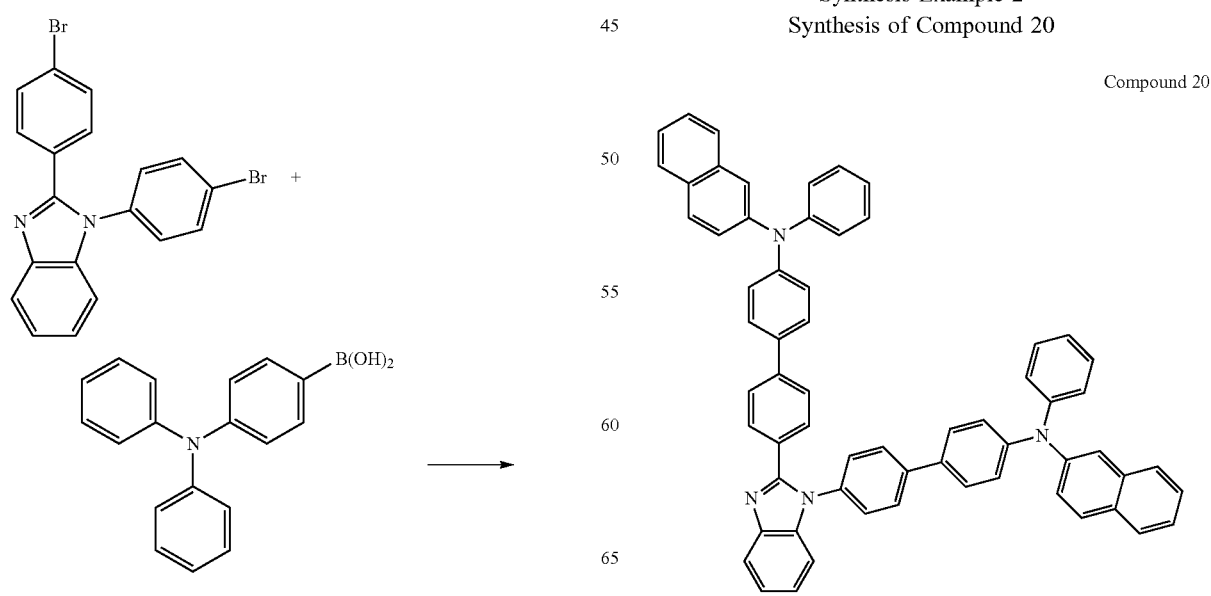

Compound 20 was synthesized in the same manner as in the synthesis of Compound 18, except that 4-(2-naphthylphenylamino)phenylboroic acid, instead of 4-(diphenylamino)phenylboroic acid, was used.

$^1$H NMR (400 MHz, CDCl3) δ 7.70 (2H), 7.55 (2H), 7.54 (4H), 7.51 (2H), 7.50 (2H), 7.44 (2H), 7.30 (2H), 7.26 (2H), 7.23 (6H), 7.09 (2H), 7.01 (4H), 6.79 (4H), 6.52 (4H), 6.46 (4H).

MALDI-TOF MS: calcd for C63H44N4 856.36 g/mol. found 857.05 g/mol.

Synthesis Example 3

Synthesis of Compound 22

Compound 22

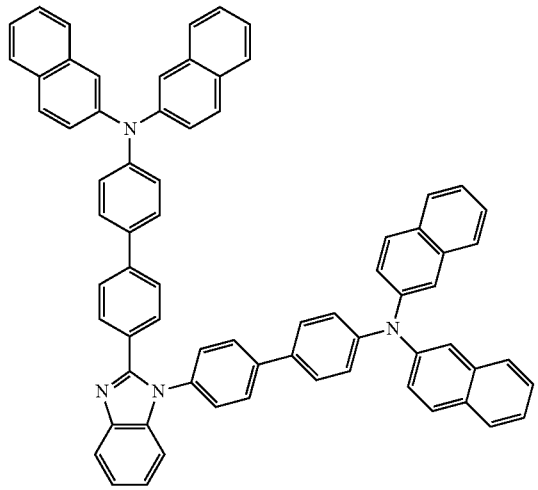

Compound 22 was synthesized in the same manner as in the synthesis of Compound 18, except that 4-(di-2-naphthylamino)phenylboroic acid, in instead of 4-(diphenylamino)phenylboroic acid, was used.

$^1$H NMR (400 MHz, CDCl3) δ 7.70 (2H), 7.55 (4H), 7.54 (4H), 7.51 (4H), 7.50 (2H), 7.44 (4H), 7.30 (2H), 7.26 (2H), 7.23 (8H), 7.09 (4H), 6.79 (4H), 6.76 (4H), 6.52 (4H).

MALDI-TOF MS: calcd for C71H48N4 956.39 g/mol. found 957.17 g/mol.

Synthesis Example 4

Synthesis of Compound 23

Compound 23

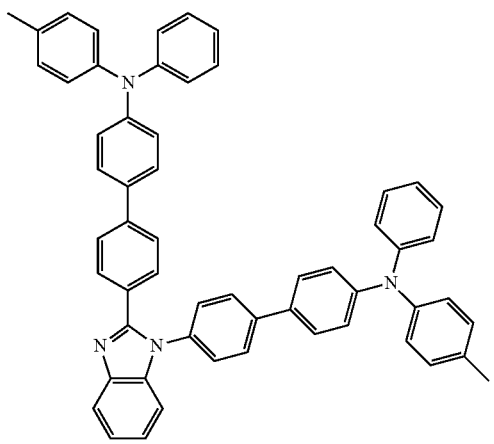

Compound 23 was synthesized in the same manner as in the synthesis of Compound 18, except that 4-(4-methylphenyl-phenylamino)phenylboroic acid, in instead of 4-(diphenylamino)phenylboroic acid, was used.

$^1$H NMR (400 MHz, CDCl3) δ 7.70 (2H), 7.55 (4H), 7.50 (2H), 7.30 (2H), 7.26 (2H), 7.23 (4H), 7.01 (4H), 6.81 (4H), 6.62 (2H), 6.52 (4H), 6.46 (4H), 6.34 (4H), 2.35 (6H).

MALDI-TOF MS: calcd for C57H44N4 784.36 g/mol. found 784.99 g/mol.

Additional compounds were synthesized from appropriate intermediate materials, according to the same synthetic pathways and the same method as described above.

It should be apparent for one of ordinary skill in the art to synthesize other compounds not disclosed in the above-described examples, based on the above-described synthetic pathways and source materials.

Example 1

An ITO glass substrate (50×50 mm, 15Ω/□, available from SAMSUNG-Corning) for organic light-emitting devices was ultrasonically washed using distilled water and then isopropanol, followed by UV ozone cleaning for about 30 minutes. The washed glass substrate with transparent electrode lines attached was loaded onto a substrate holder, and NPB (N,N'-bis(naphthalen-1-yl)-N,N'-bis(phenyl)benzidine) as a hole transport layer material was deposited via resistive heating to cover the transparent electrode lines, thereby forming a layer having a thickness of about 40 nm. Next, TCTA (4,4',4"-tris(carbazol-9-yl)triphenylamine) as a hole transport material was deposited by the same deposition method as above to form a layer having a thickness of about 20 nm. After Compound 18 obtained in Synthesis Example 1 was deposited on the layer to form an EML having a thickness of about 40 nm, TPBI (2,2',2"-(1,3,5-benzinetriyl)-tris(1-phenyl-1-Hbenzimidazole)) as an ETL material was deposited on the EML to form an ETL having a thickness of about 20 nm. LiF and Al were sequentially deposited on the ETL to a thickness of about 1 nm and about 100 nm, respectively, to form a metal electrode, thereby completing the manufacture of the organic light-emitting material. A Suicel plus 200 system (available from Sunic System Co., ltd.) was used for the deposition processes.

Example 2

An organic light-emitting device was manufactured in the same manner as in Example 1, except that Compound 20, instead of Compound 18, was used.

Example 3

An organic light-emitting device was manufactured in the same manner as in Example 1, except that Compound 22, instead of Compound 18, was used.

Example 4

An organic light-emitting device was manufactured in the same manner as in Example 1, except that Compound 23, instead of Compound 18, was used.

Comparative Example 1

An organic light-emitting device was manufactured in the same manner as in Example 1, except that β-ADN, instead of Compound 18, was used.

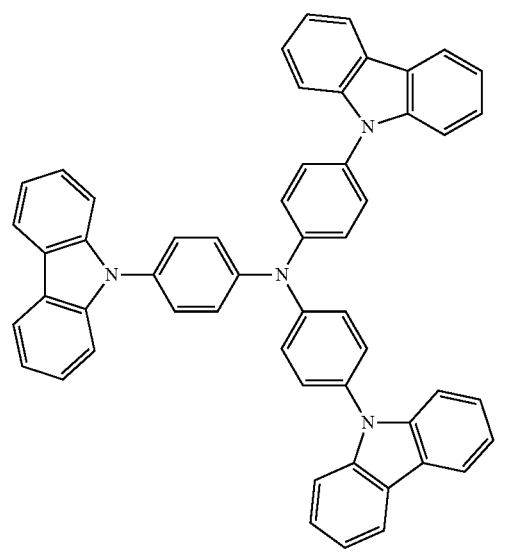

TCTA

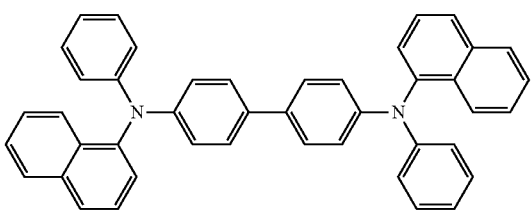

NPB

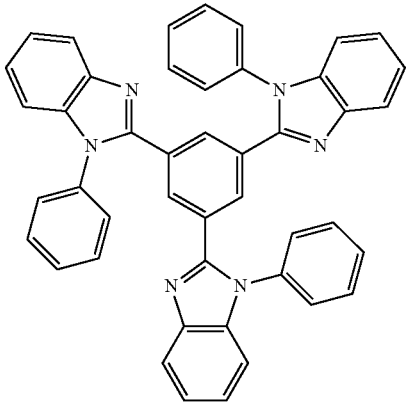

TPBI

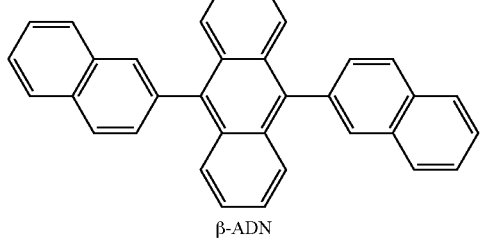

β-ADN

Comparative Example 2

An organic light-emitting device was manufactured in the same manner as in Example 1, except that Compound 73, instead of Compound 18, was used.

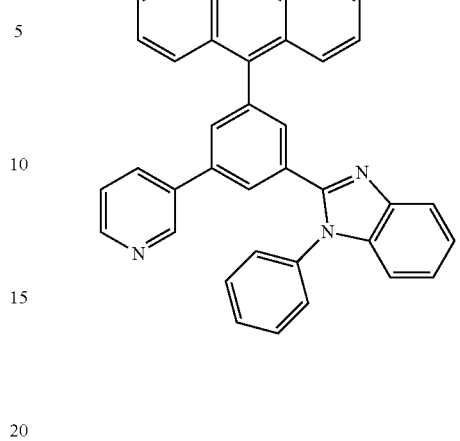

Compound 73

The organic light-emitting devices manufactured using the compounds of Formula 1 above according to embodiments as EML materials had significantly lower driving voltages and improved I-V-L characteristics, compared to the organic light-emitting device of Comparative Example 1 manufactured using a suitable material β-ADN. Typical characteristics of the organic light-emitting devices of Examples 1 to 4 and Comparative Examples 1 and 2 are summarized in Table 1 below.

TABLE 1

| @ 100 nit | Current density (mA/cm$^2$) | Quantum efficiency (%) | CIE (x, y) | EL λmax |
|---|---|---|---|---|
| Example 1 | 3.1 | 4.7 | 0.15, 0.08 | 452 |
| Example 2 | 2.6 | 4.9 | 0.15, 0.09 | 454 |
| Example 3 | 2.0 | 5.2 | 0.14, 0.11 | 458 |
| Example 4 | 3.3 | 4.4 | 0.14, 0.08 | 452 |
| Comparative Example 1 | 5.2 | 2.7 | 0.15, 0.07 | 452 |
| Comparative Example 2 | 3.3 | 2.9 | 0.15, 0.12 | 460 |

As described above, according to the one or more of the above embodiments of the present invention, an organic light-emitting device with high efficiency and improved lifetime characteristics may be manufactured including a heterocyclic compound of Formula 1 above, as an arylamine derivative having a benzimidazole backbone, in an emission layer of the organic light-emitting device. The heterocyclic compound of Formula 1 may be used in a full-color display.

It should be understood that the example embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the drawing, it will be understood by those of ordinary skill in the art that various changes in form and details may be made therein without departing from the spirit and scope of the present invention as defined by the following claims, and equivalent thereof.

What is claimed is:

1. A heterocyclic compound represented by Formula 1 below:

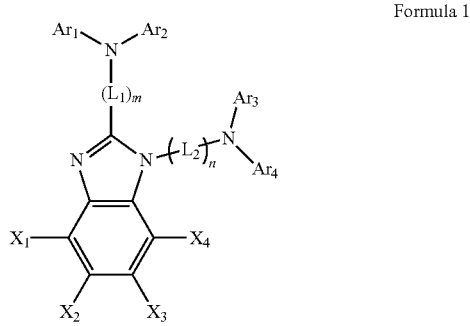

Formula 1 wherein, in Formula 1 above, $X_1$ to $X_4$ are each independently a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C3-C10 cycloalkenyl group, a substituted or unsubstituted C3-C10 heterocycloalkyl group, a substituted or unsubstituted C3-C10 heterocycloalkenyl group, a substituted or unsubstituted C6-C60 aryl group, a substituted or unsubstituted C6-C60 aryloxy group, a substituted or unsubstituted C6-C60 arylthiol group, a substituted or unsubstituted C2-C60 heteroaryl group, —$N(Q_1)(Q_2)$, or —$Si(Q_3)(Q_4)(Q_5)$, where $Q_1$ to $Q_5$ are each independently a hydrogen atom, a C1-C10 alkyl group, a C6-C20 aryl group, or a C2-C20 heteroaryl group;

$L_1$ is a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, a substituted C2-C60 heteroarylene group, an unsubstituted pyrazolyl group, an unsubstituted imidazolyl group, an unsubstituted oxazolyl group, an unsubstituted thiazolyl group, an unsubstituted triazolyl group, an unsubstituted tetrazolyl group, an unsubstituted oxadiazolyl group, an unsubstituted pyridazinyl group, an unsubstituted pyrimidinyl group, an unsubstituted triazinyl group, an unsubstituted carbazol group, an unsubstituted indol group, an unsubstituted quinolyl group, an unsubstituted isoquinolyl group, or an unsubstituted dibenzothiophene group;

$L_2$ is a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, or a substituted or unsubstituted C2-C60 heteroarylene group;

n and m are each independently an integer from 1 to 3; and $Ar_1$ to $Ar_4$ are each independently a substituted or unsubstituted C6-C60 aryl group, or a substituted or unsubstituted C2-C60 heteroaryl group, wherein when each of $Ar_1$ to $Ar_4$ is an unsubstituted phenyl group, $X_1$ to $X_4$ are each a deuterium atom, or $(L_1)_m$ and $(L_2)_n$ are each a phenylene group.

2. The heterocyclic compound of claim 1, wherein $X_1$ to $X_4$ are each independently a hydrogen atom or a deuterium atom.

3. The heterocyclic compound of claim 1, wherein n and m in Formula 1 are each independently an integer of 1 or 2.

4. The heterocyclic compound of claim 1, wherein $L_1$ and $L_2$ in Formula 1 are each independently a group represented by Formula 2a below:

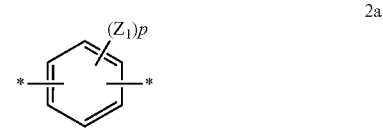

2a wherein, in Formula 2a, $Z_1$ is a hydrogen atom, a deuterium atom, a substituted or unsubstituted C1-C20 alkyl group, a substituted or unsubstituted C6-C20 aryl group, a substituted or unsubstituted C2-C20 heteroaryl group, a substituted or unsubstituted C6-C20 condensed polycyclic group, a halogen atom, a cyano group, a nitro group, a hydroxy group, a carboxy group, or $Si(Q_3)(Q_4)(Q_5)$, where $Q_3$ to $Q_5$ are each independently a hydrogen atom, a C1-C10 alkyl group, a C6-C20 aryl group, or a C2-C20 heteroaryl group;

p is an integer from 1 to 4, and when p is 2 or more, a plurality of $Z_1$s are identical to or different from each other; and

* indicates a binding site.

5. The heterocyclic compound of claim 4, wherein $Z_1$ in Formula 2a is a hydrogen atom or a deuterium atom.

6. The heterocyclic compound of claim 1, wherein $Ar_1$ to $Ar_4$ in Formula 1 are each independently a group represented by Formula 3a or 3b below:

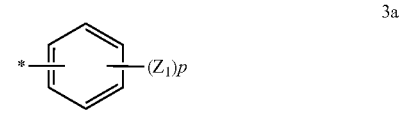

3a

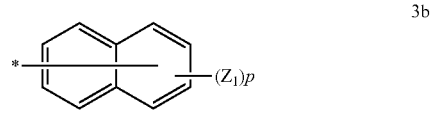

3b wherein, in Formulae 3a and 3b, $Z_1$ is a hydrogen atom, a deuterium atom, a substituted or unsubstituted C1-C20 alkyl group, a substituted or unsubstituted C6-C20 aryl group, a substituted or unsubstituted C2-C20 heteroaryl group, a substituted or unsubstituted C6-C20 condensed polycyclic group, a halogen atom, a cyano group, a nitro group, a hydroxy group, a carboxy group, or $Si(Q_3)(Q_4)(Q_5)$, where $Q_3$ to $Q_5$ are each independently a hydrogen atom, a C1-C10 alkyl group, a C6-C20 aryl group, or a C2-C20 heteroaryl group;

p is an integer from 1 to 7, and when p is two or more, a plurality of $Z_1$s are identical to or different from each other; and
* indicates a binding site.
7. The heterocyclic compound of claim 1, wherein
the heterocyclic compound of Formula 1 is one of Compounds 1 to 17 and 19 to 34 below:
Compound 1
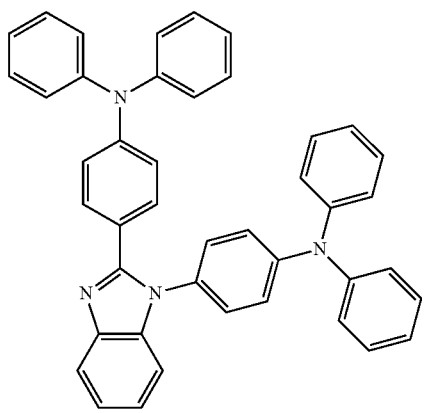
Compound 2
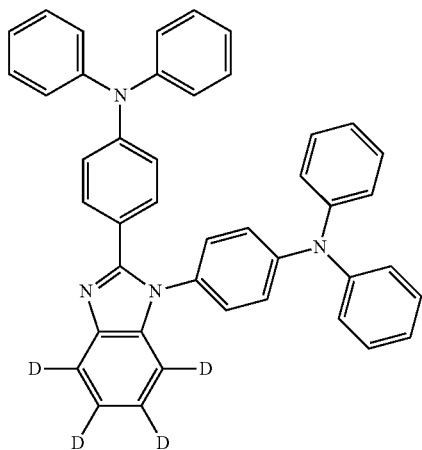
Compound 3
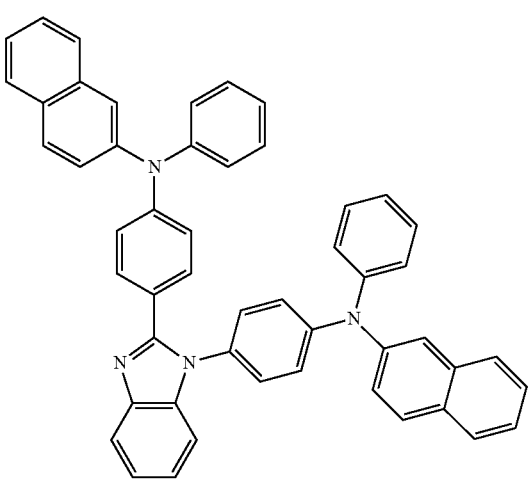
Compound 4
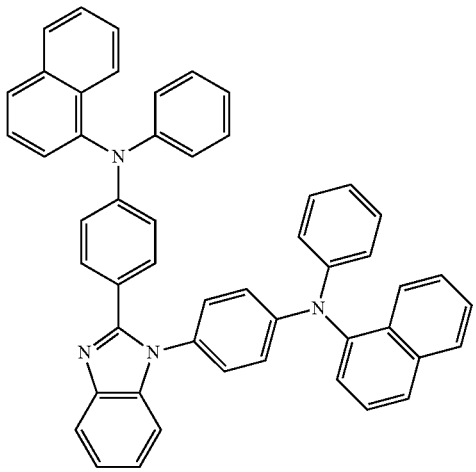
Compound 5
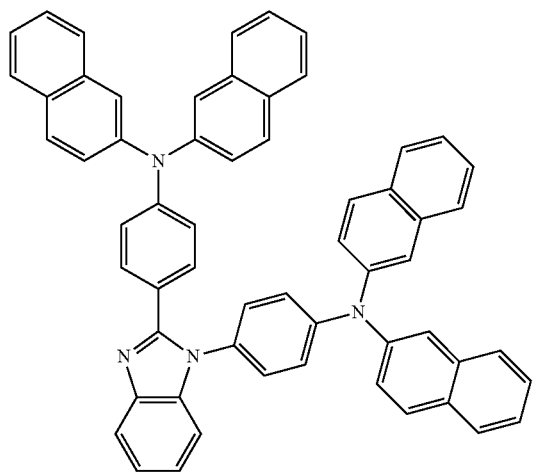
Compound 6
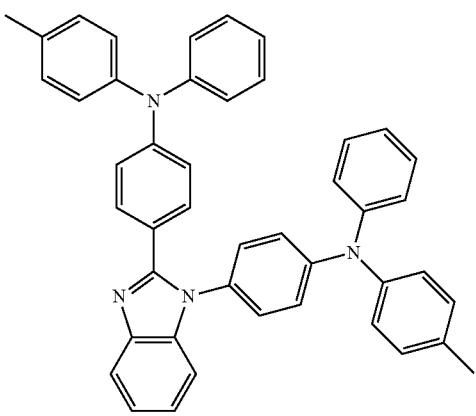

Compound 7
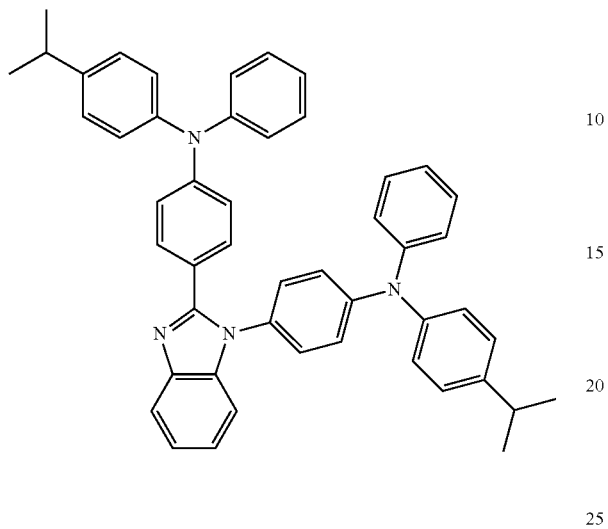
Compound 8
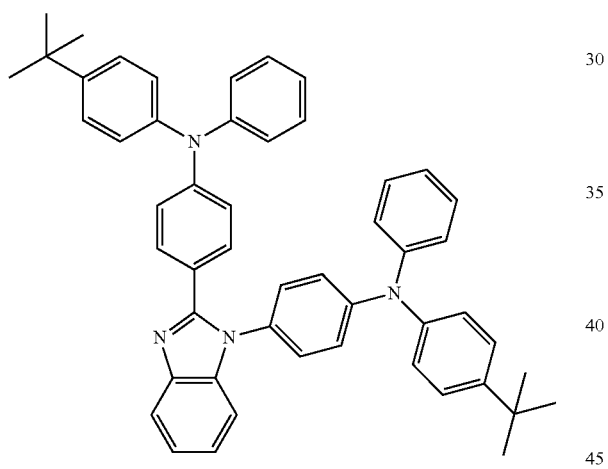
Compound 9
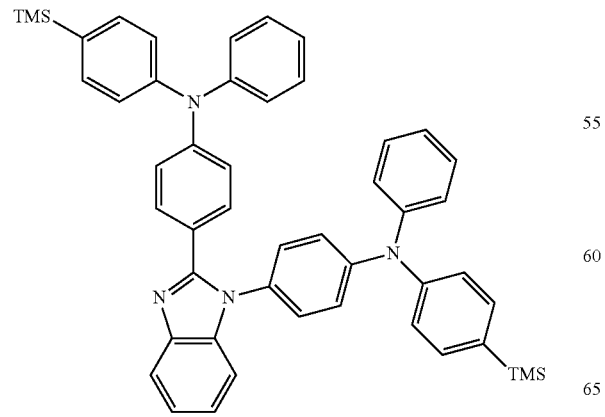
Compound 10
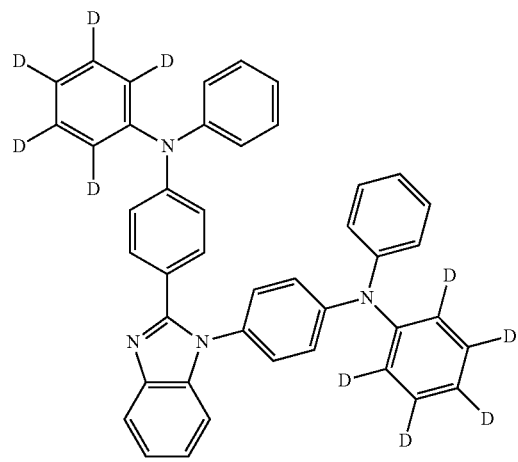
Compound 11
Compound 12
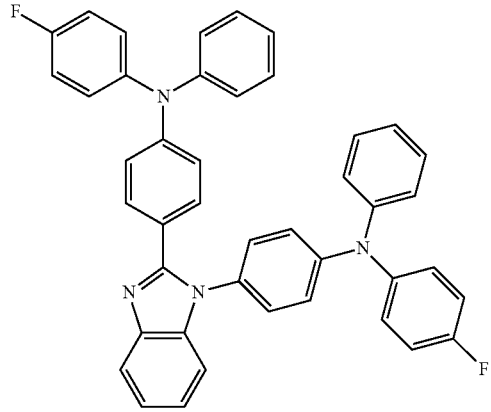

-continued
Compound 13
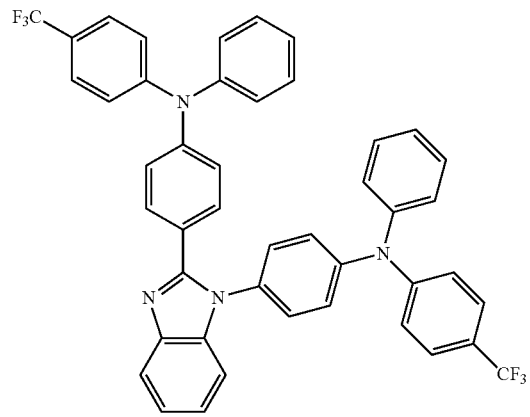
Compound 14
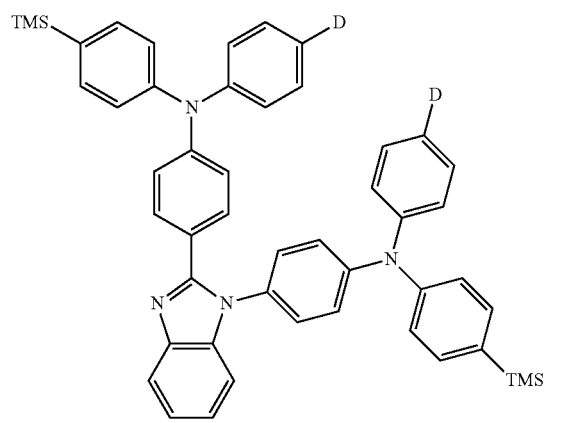
Compound 15
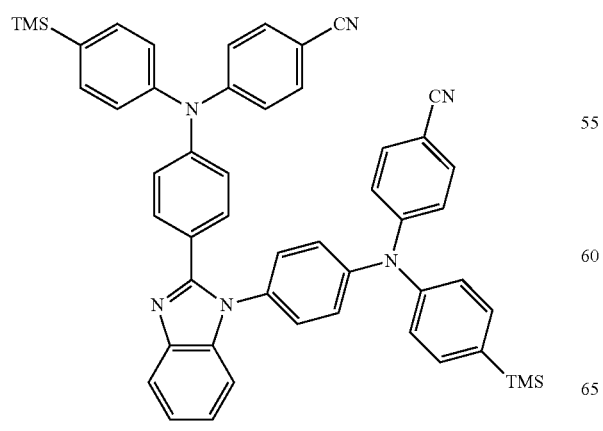
-continued
Compound 16
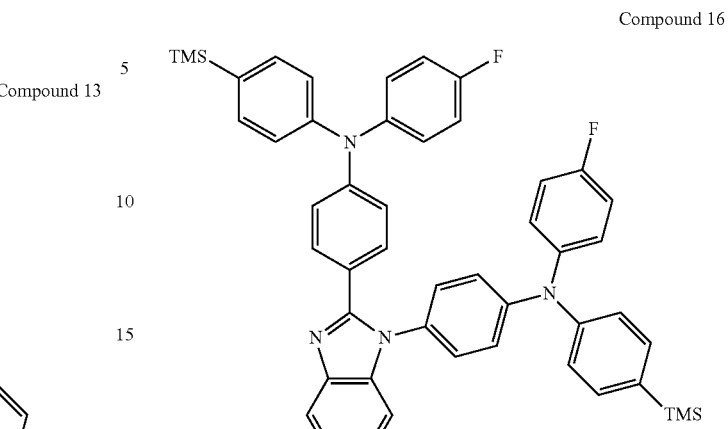
Compound 17
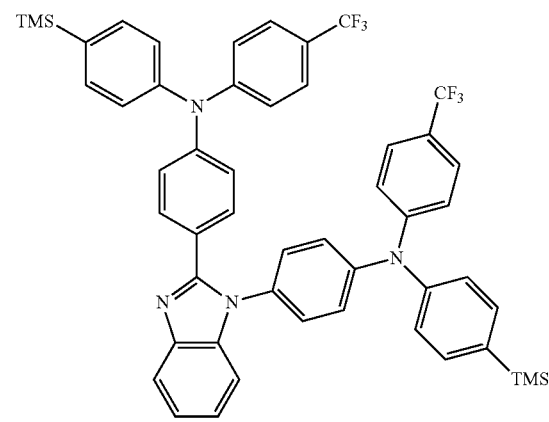
Compound 19
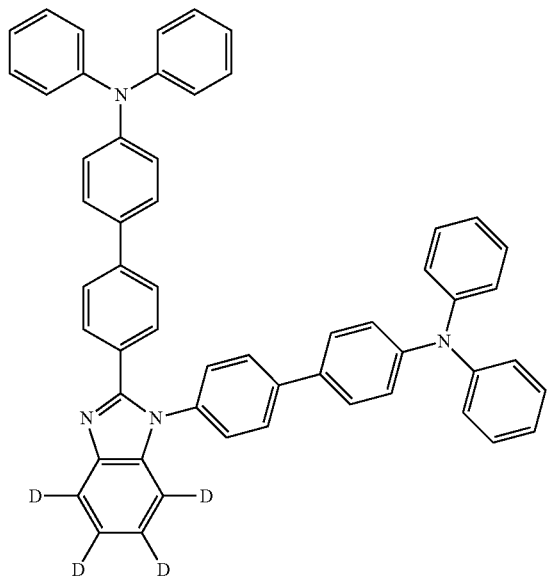

Compound 20
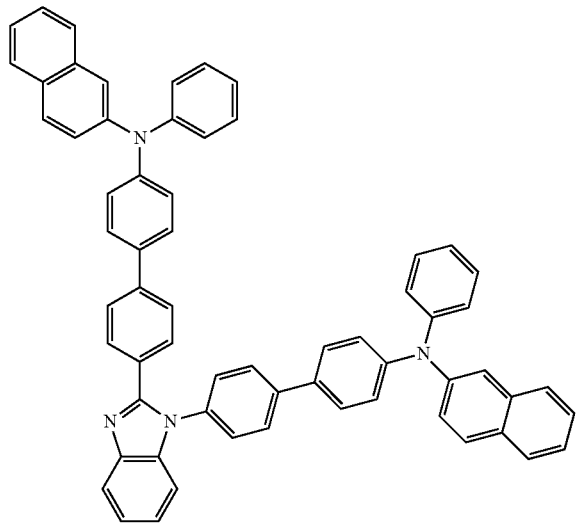
Compound 21
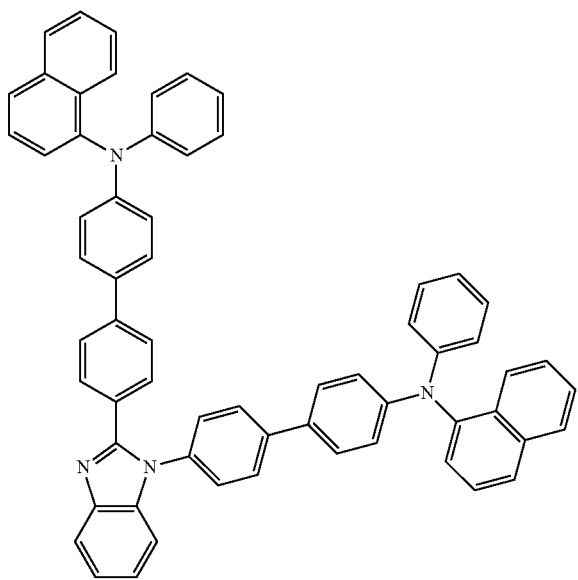
Compound 22
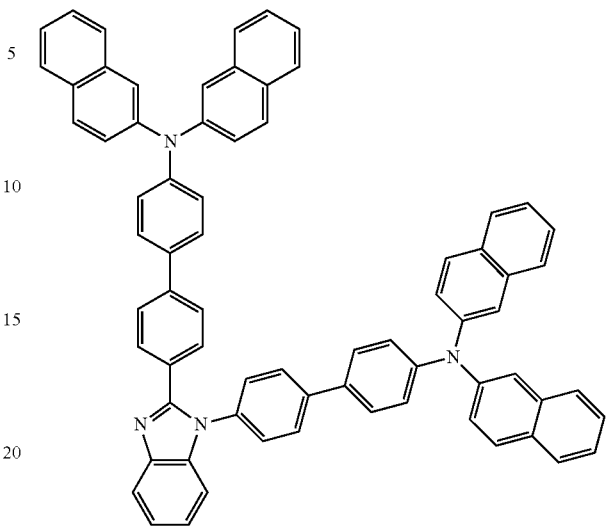
Compound 23
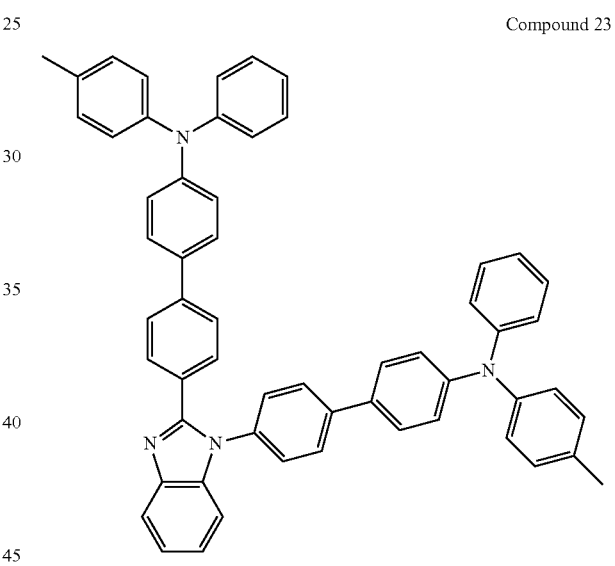
Compound 24
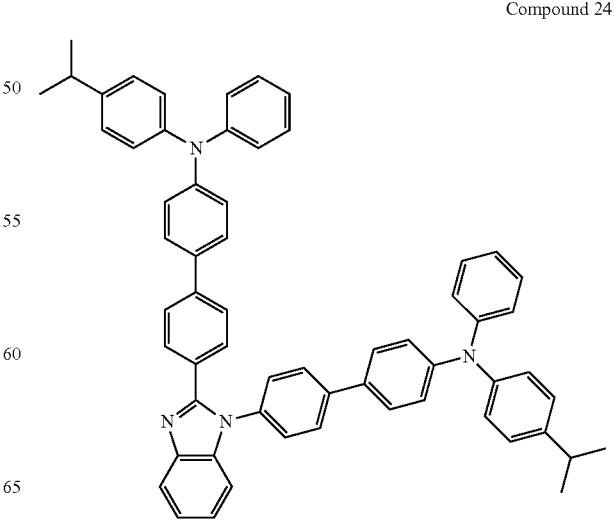

Compound 25
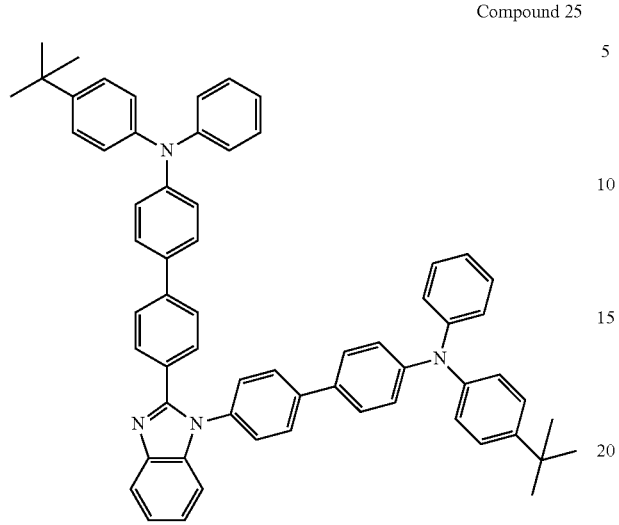
Compound 28
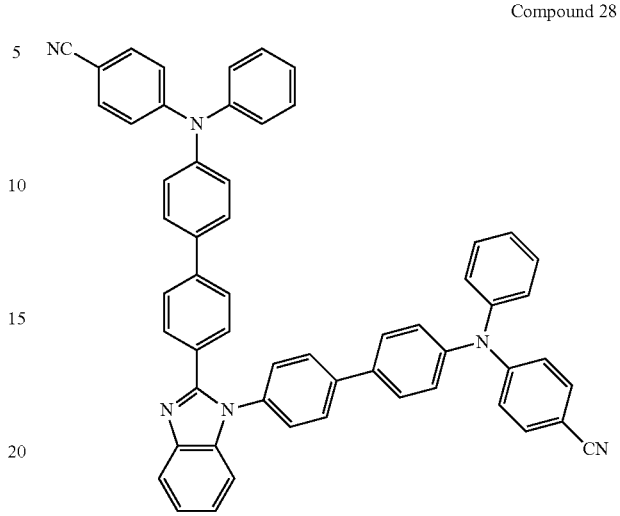
Compound 26
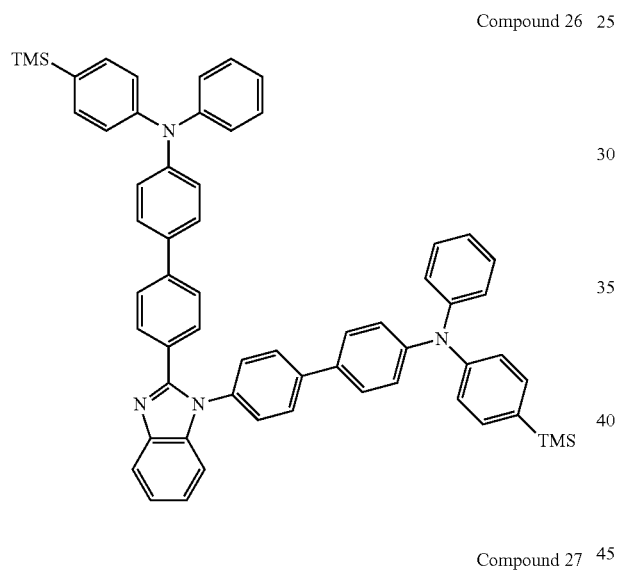
Compound 29
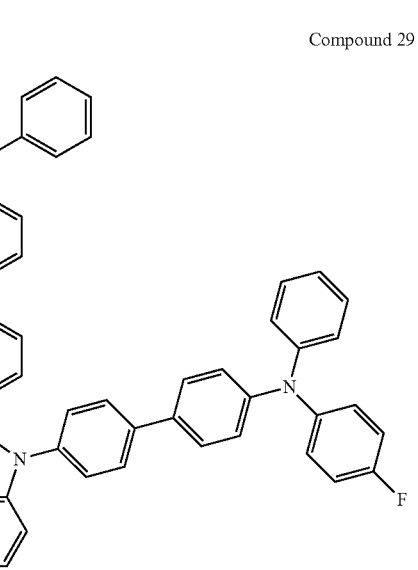
Compound 27
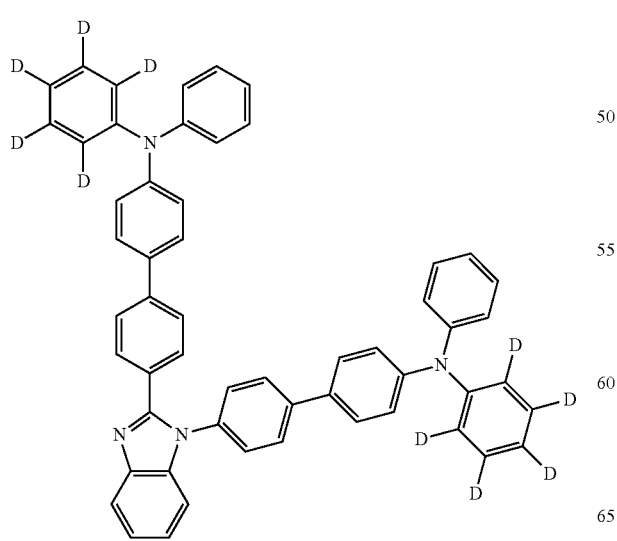
Compound 30
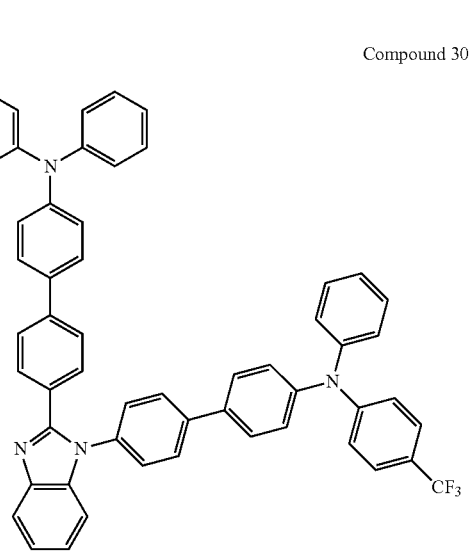

Compound 31

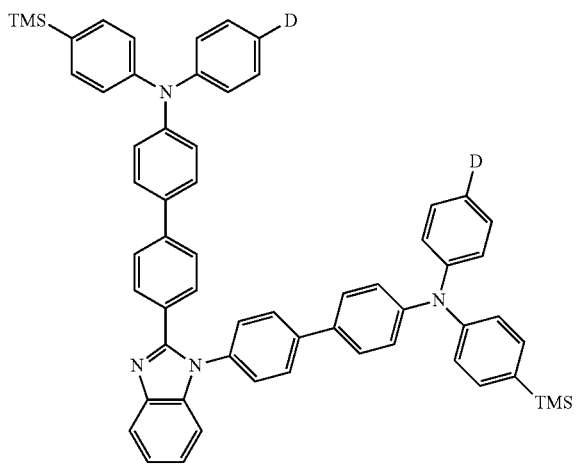

Compound 34

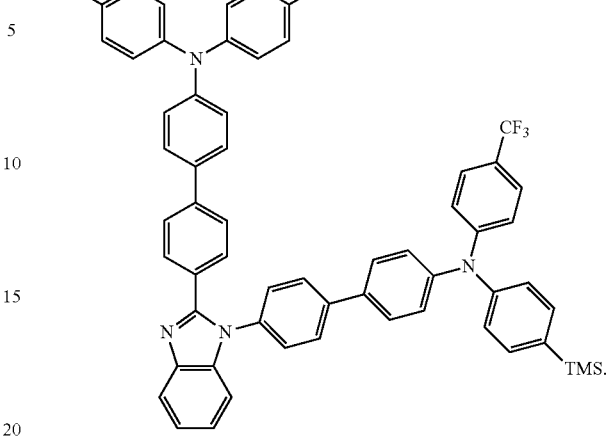

Compound 32

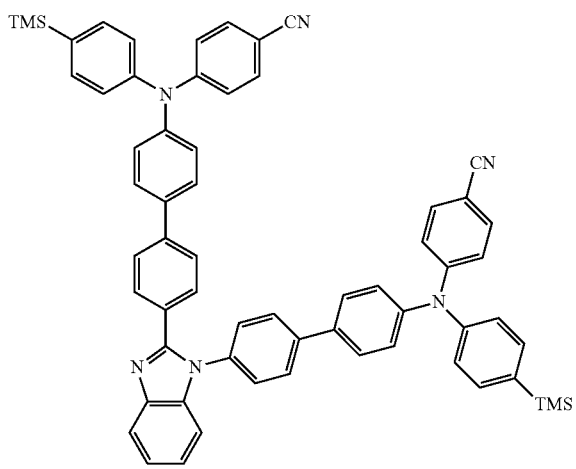

Compound 33

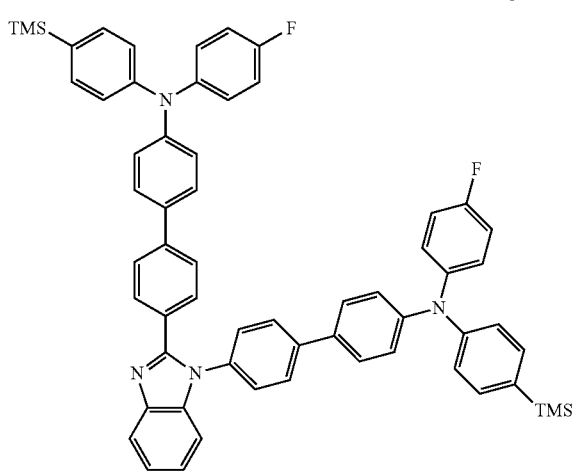

8. An organic light-emitting device comprising:
a first electrode;
a second electrode; and
an organic layer between the first electrode and the second electrode,
wherein the organic layer comprises the heterocyclic compound of claim 1.

9. The organic light-emitting device of claim 8, wherein the organic layer comprises an emission layer.

10. The organic light-emitting device of claim 8, wherein the organic layer comprises a blue emission layer.

11. The organic light-emitting device of claim 8, wherein the organic layer comprises an emission layer; and an electron injection layer, an electron transport layer, a functional layer having both electron injection and transport capabilities, a hole injection layer, a hole transport layer, or a functional layer having both hole injection and transport capabilities, and
the emission layer comprises an anthracene-based compound, an arylamine-based compound, or a styryl-based compound.

12. The organic light-emitting device of claim 8, wherein the organic layer comprises an emission layer; and an electron injection layer, an electron transport layer, a functional layer having both electron injection and transport capabilities, a hole injection layer, a hole transport layer, or a functional layer having both hole injection and transport capabilities, and
the emission layer comprises red, green, blue, and white emission layers, one of which comprises a phosphorescent compound.

13. The organic light-emitting device of claim 12, wherein the organic layer comprises at least one of the hole injection layer, the hole transport layer, and the functional layer having both hole injection and hole transport capabilities, and the at least one of the hole injection layer, the hole transport layer, and the functional layer having both hole injection and hole transport capabilities comprises a charge-generating material.

14. The organic light-emitting device of claim 13, wherein the charge-generating material is a p-type dopant.

15. The organic light-emitting device of claim 14, wherein the p-dopant is a quinone derivative.

16. The organic light-emitting device of claim 14, wherein the p-dopant is a metal oxide.

17. The organic light-emitting device of claim 14, wherein the p-dopant is a cyano group-containing compound.

18. The organic light-emitting device of claim 8, wherein the organic layer comprises an electron transport layer, and the electron transport layer comprises a metal complex.

19. The organic light-emitting device of claim 8, wherein the organic layer comprises the heterocyclic compound of claim 1 formed by a wet process.

20. A flat panel display device comprising the organic light-emitting device of claim 8, wherein the first electrode of the organic light-emitting device is electrically connected to a source electrode or a drain electrode of a thin-film transistor.

21. A heterocyclic compound represented by Formula 1 below:

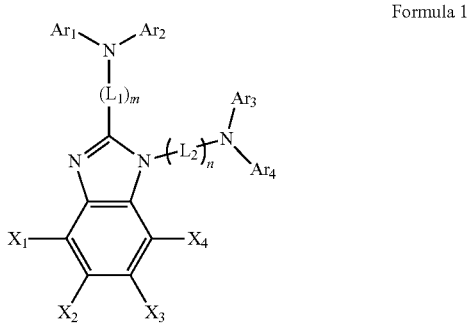

Formula 1 wherein, in Formula 1 above, $X_1$ to $X_4$ are each independently a hydrogen atom, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted C1-C60 alkyl group, a substituted or unsubstituted C2-C60 alkenyl group, a substituted or unsubstituted C2-C60 alkynyl group, a substituted or unsubstituted C1-C60 alkoxy group, a substituted or unsubstituted C3-C10 cycloalkyl group, a substituted or unsubstituted C3-C10 cycloalkenyl group, a substituted or unsubstituted C3-C10 heterocycloalkyl group, a substituted or unsubstituted C3-C10 heterocycloalkenyl group, a substituted or unsubstituted C6-C60 aryl group, a substituted or unsubstituted C6-C60 aryloxy group, a substituted or unsubstituted C6-C60 arylthiol group, a substituted or unsubstituted C2-C60 heteroaryl group, —N($Q_1$)($Q_2$), or —Si($Q_3$)($Q_4$)($Q_5$), where $Q_1$ to $Q_5$ are each independently a hydrogen atom, a C1-C10 alkyl group, a C6-C20 aryl group, or a C2-C20 heteroaryl group;

$L_1$ is a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, a substituted C2-C60 heteroarylene group, an unsubstituted pyrazolyl group, an unsubstituted imidazolyl group, an unsubstituted oxazolyl group, an unsubstituted thiazolyl group, an unsubstituted triazolyl group, an unsubstituted tetrazolyl group, an unsubstituted oxadiazolyl group, an unsubstituted pyridazinyl group, an unsubstituted pyrimidinyl group, an unsubstituted triazinyl group, an unsubstituted carbazol group, an unsubstituted indol group, an unsubstituted quinolyl group, an unsubstituted isoquinolyl group, or an unsubstituted dibenzothiophene group;

$L_2$ is a substituted or unsubstituted C3-C10 cycloalkylene group, a substituted or unsubstituted C3-C10 cycloalkenylene group, a substituted or unsubstituted C3-C10 heterocycloalkylene group, a substituted or unsubstituted C3-C10 heterocycloalkenylene group, a substituted or unsubstituted C6-C60 arylene group, or a substituted or unsubstituted C2-C60 heteroarylene group;

n and m are each independently an integer from 1 to 3; and $Ar_1$ to $Ar_4$ are each independently a substituted or unsubstituted C6-C60 aryl group, or a substituted or unsubstituted C2-C60 heteroaryl group, wherein when each of $Ar_1$ to $Ar_4$ is an unsubstituted phenyl group, each of $X_1$ to $X_4$ is a deuterium atom, or at least one of $(L_1)_m$ and $(L_2)_n$ is not a bi-phenylene group.

* * * * *